US008569038B2

(12) United States Patent
Takahashi

(10) Patent No.: US 8,569,038 B2
(45) Date of Patent: Oct. 29, 2013

(54) TRANSFORMANT HAVING AN INCREASED FREQUENCY OF HOMOLOGOUS RECOMBINATION

(75) Inventor: Tadashi Takahashi, Noda (JP)

(73) Assignee: Kikkoman Corporation, Noda-Shi (JP)

( * ) Notice: Subject to any disclaimer, the term of this patent is extended or adjusted under 35 U.S.C. 154(b) by 1553 days.

(21) Appl. No.: 11/292,071

(22) Filed: Dec. 2, 2005

(65) Prior Publication Data

US 2006/0183233 A1 Aug. 17, 2006

(30) Foreign Application Priority Data

Dec. 6, 2004 (JP) ................................ 2004-353026

(51) Int. Cl.
*C12N 1/00* (2006.01)
*C12N 15/00* (2006.01)

(52) U.S. Cl.
USPC ..................... 435/254.3; 435/243; 435/254.1; 435/254.11; 435/256.1; 435/440

(58) Field of Classification Search
None
See application file for complete search history.

(56) References Cited

U.S. PATENT DOCUMENTS 5,707,847 A * 1/1998 Christgau et al. ............. 435/197
6,569,681 B1 5/2003 Ivanov
7,122,320 B2 * 10/2006 Reiter et al. ................... 435/7.1
7,732,208 B2 * 6/2010 Inoue ............................ 435/471
7,794,962 B2 * 9/2010 Emalfarb et al. ............ 435/7.31
2004/0073967 A1 * 4/2004 Hooykaas et al. ............ 800/278

FOREIGN PATENT DOCUMENTS

EP 1 384 782 A1 1/2004
WO WO 01 068882 9/2001
WO WO-02 079476 A1 10/2002
WO WO 2005095624 * 10/2005

OTHER PUBLICATIONS

Ninimiya et al., Proc. Natl. Acad. Sci. USA 101:12248-12252, 2004.*
Kooistra et al. , Yeast 21:781-792, 2004.*
Laging et al. Nucl. Acids. Res. 29 (2) e8, 2001.*
Natsume, Toyoaki et al., Bioscience Biotechnol. Biochem., vol. 68, No. 8, pp. 1649-1656 (2004).
Database accession No. AB177394; XP-002371829; "Neurospora crassa mus-51 gene for MUS51, complete cds."; Apr. 19, 2004.
Database accession No: AB177395; XP-002371830; "Neurospora crassa mus-52 gene for MUS52, complete cds."; Apr. 19, 2004.
Chaveroche, Marie-Kim et al.; Nucleic Acids Research, vol. 28, No. 22, p. E97 (XP002371804); Nov. 15, 2000.
Database accession No. CO134302; XP002371831, Jun. 18, 2004.
Database accession No: ABZ56286; XP-002371832; Mar. 28, 2003.
Krappmann, Sven et al. ; Eukaryotic Cell, vol. 5, No. 1, pp. 212-215, Jan. 2006.
Da Silva Ferreira, Marcia-Eliana et al.; Eukaryotic Cell., vol. 5, No. 1, pp. 207-211 (Jan. 2006).
Boulton, Simon J. et al; Nucleic Acids Research, vol. 24, No. 23, pp. 4639-4648 (1996).
Nussenzweig, Andre et al.; Nature, vol. 382, pp. 551-555 (1996).
Hsu, Hsin-Ling et al.; Genes & Development, vol. 14, pp. 2807-2812 (2000).
Bundock, Paul et al.; Nucleic Acids Research, vol. 30, No. 15, pp. 3395-3400 (2002).
Gallego, M.E. et al.; The Plant Journal, vol. 35, pp. 557-565 (2003).
Kooistra, Rolf et al.; Yeast, vol. 21, pp. 781-792 (2004).
Ninomiya, Yuuko et al.; PNAS, vol. 101, pp. 12248-12253 (2004).
Takahashi, T. et al.; Molecular Genetics and Genomics, pp. 1-19 (2004).

* cited by examiner

*Primary Examiner* — Jennifer Dunston
*Assistant Examiner* — Nancy J Leith
(74) *Attorney, Agent, or Firm* — Birch, Stewart, Kolasch & Birch, LLP

(57) ABSTRACT

The purpose of the present invention is to provide a strain having a significantly increased frequency of homologous recombination, which is necessary for gene disruption of gene replacement by gene targeting of a mitosporic filamentous fungus. This invention relates to a transformant having an increased frequency of homologous recombination (gene targeting), which is a mitosporic filamentous fungus belonging to Trichocomaceae, due to suppression of a ku gene by ku gene disruption or antisense RNA method, to a method for the production of a gene-disruption stain, gene-deletion strain, gene-replacement strain, gene-insertion strain or chromosome-modification strain by means of the gene targeting method using said transformant, and to the above-mentioned ku genes such as those derived from *Aspergillus sojae* and *Aspergillus oryzae*, and their expressed products (proteins).

4 Claims, 10 Drawing Sheets

Lane 1 : Parent strain (I-6), Lane 3 : ku70-disruption strain,
Lane 2 & 4-8 : Non-disruption strains, M : Molecular markers Lane 1 & 3: Ku70-insertion strain (*ku70::ptrA*),
Lane 2 : ku70-disruption strain (*ku70::pyrG*),
M : Molecular markers Lane 1 : Parent strain (I-6),
Lane 2-4 : tannase-disruption strain,
M : Molecular markers Lane 1 &2: ku80-disruption strain,
Lane 3 &4 : Non-disruption strain,
M : Molecular markers Lane 1: *A. oryzae* ku70-disruption strain,
Lane 2-4: Non-disruption strains,
M : Molecular markers

TRANSFORMANT HAVING AN INCREASED FREQUENCY OF HOMOLOGOUS RECOMBINATION

TECHNICAL FIELD

The present invention relates to a transformant (variant strain) having a significantly increased frequency of homologous recombination, which is a mitosporic filamentous fungus belonging to Trichocomaceae, for example, *Aspergillus* such as *Aspergillus sojae* and *Aspergillus oryzae*. The present invention also relates to genetic engineering or manipulating methods using the transformant as a host.

The present invention further relates to genes and their expressed products involved in non-homologous recombination such as ku70 and ku80 derived from *Aspergillus sojae* and *Aspergillus oryzae.*

BACKGROUND OF THE INVENTION

It is known that a foreign DNA will be integrated into chromosome via repairing mechanism at the time of double-strand break (DSB) of chromosomal DNA. There are two kinds of mechanisms in the repairing, that is, homologous recombination and non-homologous recombination (non-homologous end joining). The integration will occur through a region having homology with the foreign DNA in the case of the homologous recombination. On the other hand, the integration will do at a random site of the chromosome regardless of a sequence of the foreign DNA in the case of the non-homologous recombination. It is conceived that the two recombination mechanisms will function in equilibration (Ristic et al., Nucl. Acids Res. (2003) 31:5229-5237).

A series of genes belonging to a so-called "rad52 group" take an essential role in the homologous recombination, which includes rad50, 51, 52, 54, Mrell and XRS2 (Kooistra et al. 2004). The homologous recombination mechanism has been confirmed to exist in a wide range of organisms from bacteria to eucaryotic organisms. A uvsC gene has been cloned and studied using *Aspergillus nidulans*, an experimental strain belonging to *Aspergillus*, having a mononuclear conidium (van Heemst et al., Mol. Gen. Genet (1997) 254: 654-64), and it was reported that the frequency of the homologous recombination would be improved by increasing expression frequency of the above genes up to a certain level.

On the other hand, it has been revealed that the non-homologous recombination will proceed with non-homologous end joining mechanism that is completely different form the homologous recombination mechanism. Genes such as ku70, ku80, Xrcc4, LIG4 and DNAPKcs are known to take an essential role in this recombination mechanism. It is known that Ku70 and Ku80 will act as a hetero dimmer, form a complex with a nucleotide kinase (XRCC4) and DNA Ligase IV, and promote the non-homologous end joining by joining with a DNA end at the time of cleavage of the DNA double-strand break for its repairing (Walker et al., Nature (2001) 412:607-614). The non-homologous recombination via ku gene has been recognized only in eucaryotic organisms.

Changes in phenotype due to the mutation or disruption of the ku gene have been reported in yeast, animal cells, plant cells, etc. The disruption of the ku gene would cause temperature-sensitiveness in *Saccharomyces cerevisiae* (Silmon et al., 1996: Non-Patent Document 1), aplasia and smallness in mice (Nussenzweig et al., 1996: Non-Patent Document 2), and binding to telomere ends and involvement in keeping their stability in human (Hsu et al 2000: Non-Patent Document 3). Furthermore, it is known that the disruption of the ku gene would increase telomere length and sensitivity against MMS in plant (Bundock et al., 2002: Non-Patent Document 4). It is also known that the ku gene would not affect non-homologous recombination via T-DNA (Gallego et al., 2003: Non-Patent Document 5). It is then deduced from the above documents that it is virtually impossible to predict the results of disruption of the ku gene because it can cause various changes in phenotypes.

Recently, it was reported that mutation in the ku gene would increase the targeting frequency in yeast of *Kluyveromayces lactis* (Kooistra et al., 2004: Non-Patent Document 6) and in *Neurospora crassa* (Ninomiya et al., 2004. Non-Patent Document 7). However, the yeast in Non-Patent Document 6 originally could show such a high targeting frequency as 88% when a homologous region had a length of about 600 bp, and its increase percentage was at most ten and several %. Similarly, the *Neurospora crassa* in Non-Patent Document 7 originally could show such a high targeting frequency as about 20% when a homologous region had a length of about 1 kb, and the frequency was increased at most by 5 times. The *Neurospora crassa* belongs to multinuclear fungi having sexual generation.

Japanese Patent Publication 2003-526376 (Patent Document 1) discloses a method for improving homologous recombination, by means of, for example, a ligation inhibitor at non-homologous ends such as anti-Ku antibody and Ku antisense RNA, or a homologous recombination accelerator such as Rad52 protein. However, it does not contain any actual examples, especially it does not have any disclosure or suggestion with respect to an example using filamentous fungi such as *Asperigillus.*

On the contrary, the gene targeting frequency in the case of *Aspergillus* was as very low as 1~3% even if a homologous region has about 2 kb. Accordingly, it has been recognized that it would require a lot of efforts to obtain a desired gene-disruption strain in case a screening on the basis of phenotypes was impossible (Takahashi et al., 2004: Non-Patent Document 8).

[Patent Document 1] Japanese Patent Publication 2003-526376

[Non-Patent Document 1] Silmon et al., Nucl. Acds Res. (1996) 24:4639-4684

[Non-Patent Document 2] Nussenzweig et al., Nature (1996) 382: 551-555

[Non-Patent Document 3] Hsu et al., Genes & Development (2000) 14: 2807-2812

[Non-Patent Document 4] Bundock et al., Nucl. Acids Res. (2002) 30:3395-3400

[Non-Patent Document 5] Gallego et al., Plant J (2003) 35:557-565

[Non-Patent Document 6] Kooistra et al. Yeast (2004) 21: 781-792

[Non-Patent Document 7] Ninomiya et al., PNAS (2004) 101:12248-12252

[Non-Patent Document 8] Takahashi et al., Mol. Gen. Genet. (2004) 272:344-52

*Aspergillus* strains such as *Aspergillus sojae* and *Aspergillus oryzae* are industrially used in the production of brewed food such as soy sauce, sake (rice wine), soybean paste, etc. Recently, a genomic sequence of *Aspergillus oryzae* has been identified, and functional analysis of their genes has become more important.

However, unlike *Aspergillus nidulans, niger, fumigatus* and *awamori* that have a mononuclear generation, *Aspergillus sojae* and *Aspergillus oryzae* are always kept in a multinuclear state in their whole life cycle including in a conidium condition, and their sexual generation has not yet been observed. Their nuclear-distribution mechanism from a parent cell to a daughter cell has not yet been revealed, either. Accordingly, a mutant cannot be produced by means of mating between strains or RIP (Repeat Induced Mutation), which makes it difficult to study their genetics. As a result, the genetic analysis of *Aspergillus sojae* and *Aspergillus oryzae* has fallen behind in spite of their industrially very high utility.

Gene disruption or gene-replacement by gene targeting would be a very important technique for the genetic analysis of such microorganisms as those having no sexual generation. However, there are little research reports on the homologous or non-homologous recombination mechanism with respect to the above microorganisms, and the homologous recombination frequency of *Aspergillus* strains and the like is very low. Furthermore, there exist very little foreign hetero gene markers that can be used as a marker for transfomation in these strains since they originally have high drug-resistance. As a result, it has been very difficult to obtain a strain having gene-disruption or homologous recombination at a desired site except that a screening was possible based on the phenotype. Accordingly, it has been desired to develop a method for obtaining a gene-disruption strain with a high homologous recombination frequency.

DISCLOSURE OF THE INVENTION

The present inventor prepared a transformant (variant strain) having a significantly increased frequency of homologous recombination due to suppression of the ku gene by means of gene disruption and/or antisense RNA method with use of the mitosporic filamentous fungus belonging to Trichocomaceae, for example, *Aspergillus* such as *Aspergillus sojae* and *Aspergillus oryzae*. He further examined the influence of such suppression of the gene involved in non-homologous recombination on the frequency of homologous recombination (targeting) and completed this invention.

Thus, the present invention relates to the following aspects.

(1) A transformant having an increased frequency of homologous recombination due to suppression of a ku gene, which is a mitosporic filamentous fungus belonging to Trichocomaceae.

(2) A transformant according to claim 1 that belongs to *Aspergillus*.

(3) A transformant according to claim 2 that belongs to *Aspergillus sojae* or *Aspergillus oryzae*.

(4) A transformant according to one of Claims 1-3 wherein the ku gene is disrupted.

(5) A transformant according to Claim 4 wherein the frequency of homologous recombination is increased by at least 60 times.

(6) A transformant according to one of Claims 1-3 wherein the ku gene is inactivated by antisense RNA method.

(7) A transformant according to Claim 6 wherein the frequency of homologous recombination is increased by at least 10 times.

(8) A transformant according to one of Claims 1-7 wherein the ku gene encodes one of the following proteins:

- (a) a protein consisting of an amino acid sequence represented by any one of SEQ ID NOS: 2, 4, 6, 8, 10, or 12, or
- (b) a protein consisting of an amino acid sequence of (a) wherein one or several amino acid residues are replaced, deleted, or added, and having a function relating to non-homologous recombination mechanism.

(9) A transformant according to one of Claims 1-7 wherein the ku gene consists of one of the following DNAs:

- (a) a DNA comprising a coding region represented by any one of SEQ ID NOS: 1, 3, 5, 7, 9, or 11,
- (b) a DNA being hybridized with a DNA consisting of a base sequence complementary with that of the DNA (a) under stringent conditions, and encoding a protein having a function relating to non-homologous recombination mechanism.

(10) A gene targeting method using the transformant according to one of Claims 1-9.

(11) A method for the production of a gene-disruption stain, gene-deletion strain, gene-replacement strain, gene-insertion strain or chromosome-modification strain by means of the gene targeting method of Claim 10.

(12) A ku gene encodes one of the following proteins:

- (a) a protein consisting of an amino acid sequence represented by any one of SEQ ID NOS: 2, 4, 6, 8, 10, or 12, or
- (b) a protein consisting of an amino acid sequence of (a) wherein one or several amino acid residues are replaced, deleted, or added, and having a function relating to non-homologous recombination mechanism.

(13) A ku gene consists of one of the following DNAs:

- (a) a DNA comprising a coding region represented by any one of SEQ ID NOS: 1, 3, 5, 7, 9, or 11,
- (b) a DNA being hybridized with a DNA consisting of a base sequence complementary with that of the DNA (a) under stringent conditions, and encoding a protein having a function relating to non-homologous recombination mechanism.

(14) A ku gene-expressed product of the following proteins:

- (a) a protein consisting of an amino acid sequence represented by any one of SEQ ID NOS: 2, 4, 6, 8, 10, or 12, or
- (b) a protein consisting of an amino acid sequence of (a) wherein one or several amino acid residues are replaced, deleted, or added, and having a function relating to non-homologous recombination mechanism.

According to the present invention, the transformant having an increased frequency of homologous recombination was unexpectedly obtained by suppressing the ku gene with respect to the mitosporic filamentous fungus belonging to Trichocomaceae.

The tranformant according to the present invention, especially that whose ku gene is disrupted does demonstrate a significant increase in the frequency of homologous recombination without showing any negative phenotypes such as suppression of growth and reduction of spore-forming property. Such transformant is therefore very useful for the gene targeting of *Aspergillus* strains in an efficient way, making it possible to efficiently produce various gene-disruption stains, gene-deletion strains, gene-replacement strains, gene-insertion strains or chromosome-modification strains.

BEST MODE FOR CARRYING OUT THE PRESENT INVENTION

Figure 1:
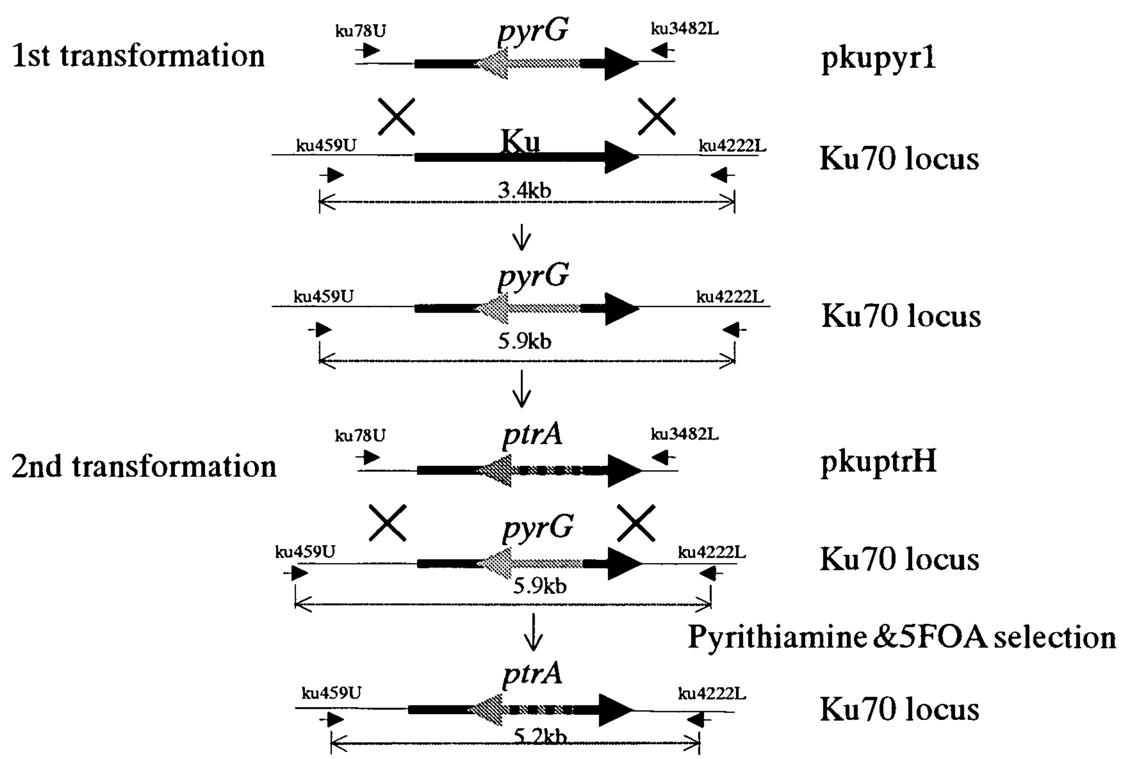
FIG. 1 is a schematic figure showing a process of the production of a ku70 gene-disruption strain.

Scope and kinds of the fungus that may be mycologically classified into the "mitosporic filamentous fungus belonging to Trichocomaceae" are obvious for those skilled in the art. There may be mentioned as representative examples strains belonging to *Aspergillus* such as *Aspergillus sojae* and *Aspergillus oryzae*, and strains belonging to *penicillium*. These strains may be commercially available from public depositories such as American Type Culture Collection (ATCC).

As already described in the above, the ku gene such as ku70 and ku80 is a gene involved in the non-homologous recombination mechanism. Its representative examples include ku70 gene (SEQ ID NO.1) and ku80 gene (SEQ ID NO.2 or SEQ ID NO.3) derived from *Aspergillus sojae*, and ku70 gene (SEQ ID NO.4) and ku80 gene (SEQ ID NO.5 or SEQ ID NO.6) derived from *Aspergillus oryzae*. Homology (identity) in an amino acid level between the above ku70 genes and between the above ku80 genes was found to be as high as 95% or more. On the other hand, the homology in an amino acid level between these genes and homologues of *Neurospora crassa* is about 50%.

Accordingly, there may be mentioned as preferable examples of the ku gene, a gene that encodes a protein consisting of an amino acid sequence represented by any one of SEQ ID NOS: 2, 4, 6, 8, 10, or 12, or a protein consisting of the same amino acid sequence wherein one or several amino acid residues are replaced, deleted, or added, and having the function relating to non-homologous recombination mechanism.

The above protein may have a high homology such as about 80% or more, preferably about 90% or more, more preferably about 95% or more on a total average to the amino acid sequence represented by any one of SEQ ID NOS: 2, 4, 6, 8, 10, or 12. The homology between the amino acid sequences may be determined by means of algorithm known to those skilled in the art such as BLAST.

Furthermore, preferable examples of the ku gene may include (a) DNA comprising a coding region represented by any one of SEQ ID NOS: 1, 3, 5, 7, 9, or 11, or DNA being hybridized with DNA consisting a base sequence complementary with that of the DNA (a) under stringent conditions, and encoding a protein having a function relating to non-homologous recombination mechanism.

The coding region in any one of SEQ ID NOS: 1, 3, 5, 7, 9, or 11 was determined based on the information about the genomic sequences of *Aspergillus sojae* and *Aspergillus oryzae*, comparison with the sequences of their homologues of *Neurospora crassa* and rules concerning an intron sequence such as GT-AG rule. The genomic sequence of the ku gene of *Aspergillus sojae* was determined by amplifying a fragment in PCR using a genomic DNA of *Aspergillus sojae* ATCC46250 as a template and primers kuU459-KuL4222 and ku2U830 and kuL4937 (prepared based on the genomic sequences of *Aspergillus oryzae* and their homologues of *Neurospora crassa*), cloning the resulting fragment by means of TOPO-TA cloning kit (Invitrogen Co.) and subjecting it to a conventional sequence determination.

The hybridization may be performed in accordance with a method known in the art, for example, that described in Current protocols in molecular biology (edited by Frederick M. Ausubel et al., 1987). When a commercially available library is used, the hybridization may be done according to instructions attached to it.

The term "stringent conditions" means in this specification, for example, those of sodium concentration of 150~900 mM, preferably 600~900 mM, pH of 6~8 at 60° C.~68° C.

The DNA that is hybridized with DNA consisting of a base sequence complementary with that of the DNA comprising a coding region represented by any one of SEQ ID NOS: 1, 3, 5, 7, 9, or 11, may include, for example, DNA consisting of a base sequence having identity (homology) with the whole base sequence of said DNA, of about 90% or more, preferably of about 95% or more on a total average. The identity between the base sequences may be determined by means of algorithm known to those skilled in the art, such as BLAST.

The suppression of the ku gene in the transformant according to the present invention may be performed by any method known to those skilled in the art such as those actually described in the examples of the present specification. For example, the ku gene may be disrupted by means of a ku gene-disruption vector, or inactivated by means of antisense RNA method using a vector expressing an antisense of the ku gene. The suppression of the ku gene may be also attained by various methods based on RNA interference. The resulting transformant may have the frequency of homologous recombination that is increased by at least 10 times, preferably by at least 60 times.

Gene targeting (targeted gene recombination) is a method for introduction of a mutation into a targeted particular gene by introducing DNA into a cell followed by selection of a homologous recombinant. Accordingly, a very high targeting rate shall be obtained by using the present transformant having an increased frequency of homologous recombination, making it possible to efficiently produce various gene-disruption stains, gene-deletion strains, gene-replacement strains, gene-insertion strains or chromosome-modification strains.

The present invention is also related to the above-mentioned ku genes such as those derived from *Aspergillus sojae* and *Aspergillus oryzae*, and their expressed products (proteins).

The transformant produced in Example 1, A ku70 strain (ASKUPTR8) derived from *Aspergillus sojae* I-6 strain (wh, ΔpyrG), was deposited at the International Patent Organism Depository of National Institute of Advanced Industrial Science and Technology at AIST Tsukuba Central 6, 1-1, Higashi 1-chome Tsukuba-shi, Ibaraki-ken 305-8566 Japan on Dec. 2, 2004 with Accession No. FERM P-20311, and then transferred to international deposit under Budapest Treaty on Nov. 17, 2005 with Accession No. FERM BP-10453.

The present invention will be specifically explained below with reference to the examples, which should not be construed to limit the scope of the present invention. Unless otherwise described, the means and conditions for gene engineering techniques in the following examples are usual ones known to those skilled in the art, such as those described in Japanese Patent Publication No. 1998-80196.

PCR may be carried out in accordance with conditions and means known to those skilled in the art by using a primer set for amplification according to the present invention. For example, the PCR is done by heating for 2 min at 94° C., followed by repeating 30 times a cycle of heating for 10 seconds at 94° C., for 20 seconds at 55° C., and for 2 min. at 72° C., and finally by for 5 min at 72° C. A usual thermal cycler such as a "9600" model manufactured by Perkin Elmer Co. may be used. A commercially available thermal resistance DNA polymerase such as ExTaq DNA polymerase (TAKARA SHUZO CO., LTD.) may be used, and the composition of a reaction mixture may be adjusted in accordance with manufacturer's instructions attached to the polymerase product. The primers used in the PCR according to the present invention are summarized in Table 3.

[Materials and Methods]

Strains:

*Aspergillus sojae* I-6 strain (wh, ΔpyrG) and *Aspergillus oryzae* RIB40 Δ pyrG strain were used. The *Aspergillus sojae* I-6 strain was a pyrG deletion strain (Takahashi et al. 2004) prepared from ATCC46250, and the *Aspergillus oryzae* RIB40 Δ pyrG strain was a pyrG deletion strain prepared from *Aspergillus oryzae* ATCC42149.

Culture Medium:

Polypeptone dextrin (PD) medium (polypepton 1%, dextrin 2%, $KH_2PO_4$ 0.5%, $NaNO_3$ 0.1%, $MgSO_4$ 0.05%, casamino acid 0.1%, pH 6.0), CzapekDox (CZ) minimum medium, and 1.2M sorbitol CZ (as regeneration medium) were used. CZ medium containing 2 mg/ml 5-fluoroortic acid (SIGMA) and 20 mM Uridine was used for positive selection of a pyrG-strain. $KClO_3$-mono-methylammonium-CZ agar plates (470 mM $KClO_3$, 100 mM mono-methylammonium, CZ) was used for negative selection of an areA C end-disruption strain. Tannic acid medium (Glucose 1%, Tannic-acid 1%, $NH_4PO_4$ 0.2%, $KH_2PO_4$ 0.2%, $MgSO_4$ 0.1%, Agar 1.5%, pH 7.5) was used for selection of Tannnase-disruption strain.

Transformation:

Conidium was inoculated on liquid PD medium (50 ml) containing 20 mM Uridine in a conical flask (150 ml) and subjected to shake culture for about 20 hours at 30° C., followed by collection of mycelium. The collected mycelium was washed with 0.7M KCl buffer, shaken gently in 0.7M KCl buffer containing 1% Lysing enzyme (Sigma Co.) for 3 hours at 30° C. to prepare protoplast. The protoplast was washed with 1.2M sorbitol buffer, and tranformed by means of a protoplast PEG method. Regeneration of the resulting transformant was carried out on 1.2M sorbitol CZ medium containing 0.5% agar.

Construction of ku70-Disruption Vector:

PCR was performed using the genomic DNA of *Aspergillus sojae* as a template, and primers ku78U and ku3482L (prepared based on the ku70 sequence of *Neurospora crassa* and its corresponding genomic sequence of *Aspergillus oryzae*). The base sequence of an amplified DNA fragment with 3.4 kb was determined to confirm that the resulting fragment comprised the ku70 gene. This fragment was cloned by means of TOPO-TA cloning kit (Invitrogen Co.). A ku fragment was excised from the resulting plasmid with EcoRI and sub-cloned into pUC18. The resulting pUC18 plasmid was cut with BglII, and ligated with a 2.7 Kb DNA fragment containing pyrG, which had been amplified using primers pyrU204Bg and pyrL2924Bg having a BglII site at their ends. This ligation gave a vector pkupyr1 wherein a 600 bp region within the ku70 had been replaced by pyrG (FIG. 1). A 2.1 Kb ptrA (pyrithiamine resistant gene) fragment having BglII end sites and ptrA that had been amplified using pPTRI (TAKARA SHUZO CO., LTD.) as a template and primers ptrBg2482U and ptrBg4443L was ligated with the pkupyr1 cut with BglII to give a vector pkuptrH wherein said 600 bp region had been replaced by ptrA (FIG. 1).

Figure 2:
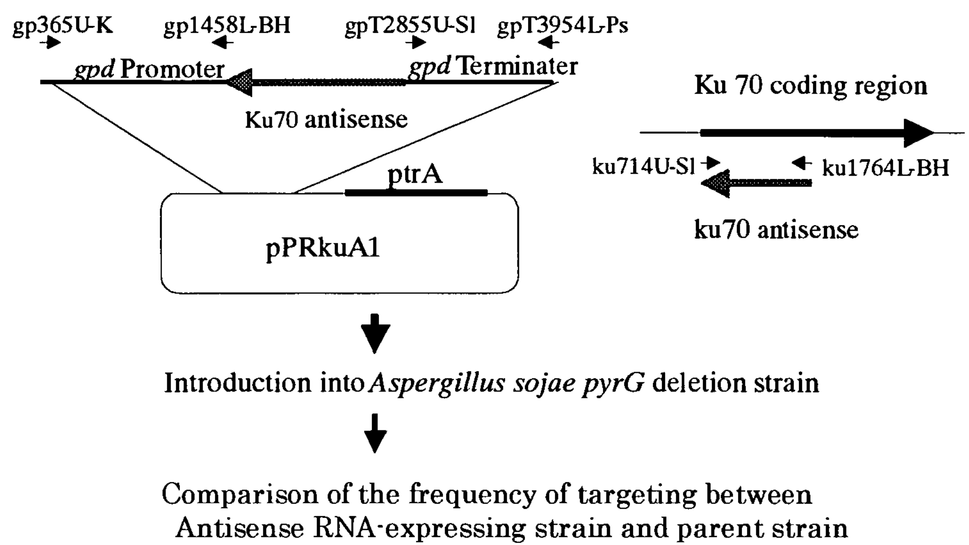
FIG. 2 is a schematic figure showing a process of the production of a ku70 antisense RNA-expressing strain.

Construction of ku70 Antisense RNA-Expressing Vector:

Sequences of a promoter and a terminator of gpdA (glycelaldehyde 3-phosphate dehydrogenase gene) were obtained from the genomic DNA of *Aspergillus sojae*, to which a 5'-end half of the coding region of the ku70 was ligated in a reverse direction to give a vector expressing ku70 antisense RNA (FIG. 2). Thus, the gpd promoter was amplified using primers gp365U-K and gp1458L-8H, cloned by means of TOPO-TA cloning kit, and sub-cloned into a KpnI-BamHI site of pUC18. Said ku fragment was amplified using primers ku714U-S1 and ku1764L-BH, cloned by means of TOPO-TA cloning kit and inserted into a BamHI-SalI site in the same vector. Finally, the gpd terminator amplified with use of primers gpT2855U-S1 and gpT3954L-Ps was inserted into a SalI-PstI site to give a construct for the expression of the ku antisense RNA. A 3 kb KpnI-PstI fragment containing the resulting construct was inserted into a KpnI-PstI site of pPTR1 to give a ku70 antisense RNA-expressing vector, pPRkuA1.

Figure 3:
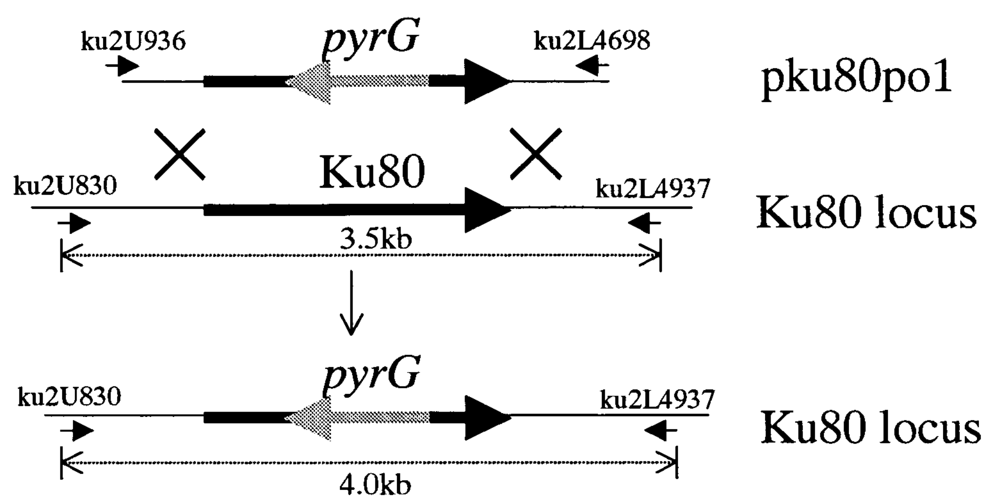
FIG. 3 is a schematic figure showing a process of the production of a ku80 gene-disruption strain.

Construction of ku80-Disruption Vector:

PCR was performed using the genomic DNA of *Aspergillus sojae* as a template, and primers ku2U936Xb and ku2L4698K (prepared based on the ku80 sequence of *Neurospora crassa* and its corresponding genomic sequence of *Aspergillus oryzae*). The base sequence of an amplified DNA fragment with 3.9 kb was determined to confirm that the resulting fragment comprised the ku80 gene. This fragment was cloned by means of TOPO-TA cloning kit (Invitrogen Co.). The resulting vector was cut with BglII-MunI and ligated with a 2.7 Kb DNA fragment containing pyrG, which had been amplified using primers pyrU204Bg and pyrL2923E, to give a ku80-disruption vector, pku80pol (FIG. 3).

Example 1

A ku70-disruption strain was prepared and the effect of ku70-disruption on the frequency of targeting (homologous recombination) was examined.

Figure 4:
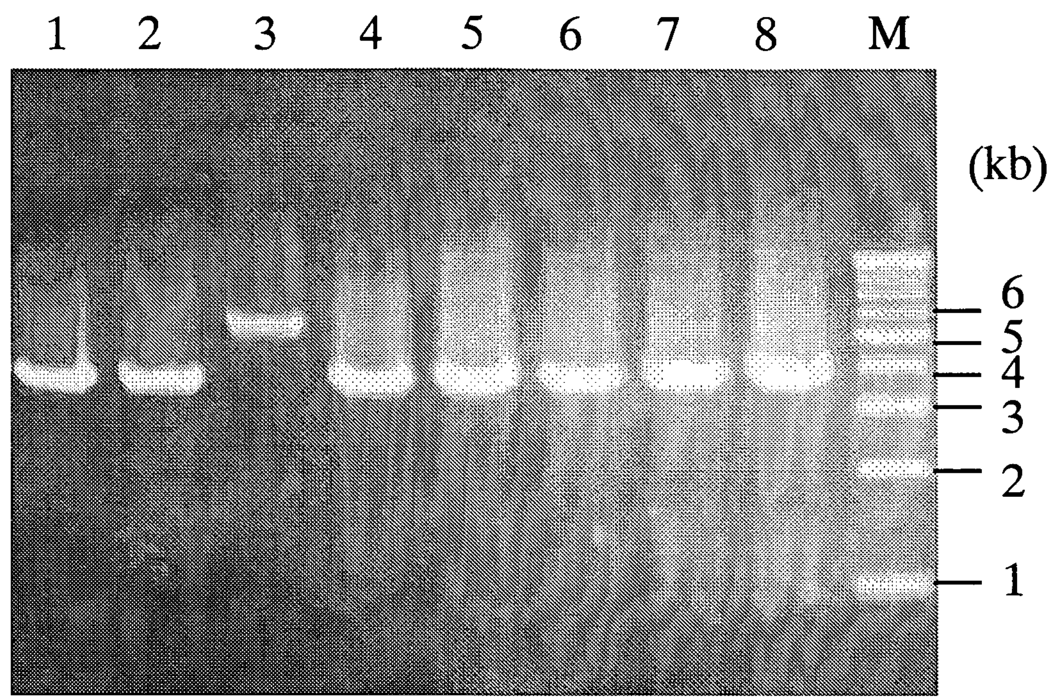
FIG. 4 is a photograph of electrophoresis showing the results of disruption of ku70 of *Aspergillus sojae*.
Figure 5:
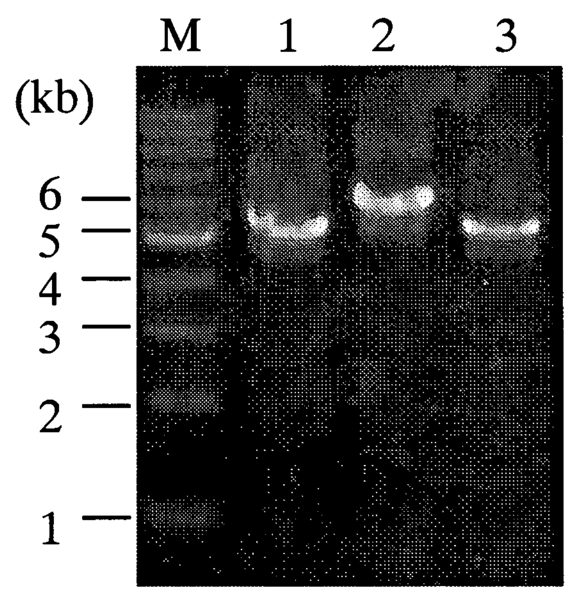
FIG. 5 is a photograph of electrophoresis showing the results of insertion of ptrA into the ku70 site of *Aspergillus sojae*.

Thus, PCR was performed using said ku70-disruption vector pkupyr1 as a template, and primers ku78U and ku3482L to amplify a DNA fragment, which was then used for transformation of the pyrG deletion strain of *Aspergillus sojae*. Genomic DNA was obtained from the transformant regenerated on 1.2M sorbitol CZ medium containing 0.5% agar, and subjected to PCR using primers kuU459-kuL4222. As a result, out of 99 transformants was obtained one ku gene-disruption strain that had an amplified fragment with a length shifted from 3.4 kb to 5.9 kb (FIG. 4). The resulting one strain was then transformed in a conventional way with a fragment obtained by amplification of the vector pkuptrH wherein pyrG had been replaced by ptrA with use of primers ku78U-3482L. After the resulting transformants were transferred to 2 mg/ml-5FOA-CZ, 5FOA-resistant strains were selected. Genomic DNA was extracted from the selected strains and subjected to PCR using primers kuU459-kuL4222. As a result, it was confirmed that 5 strains out of 12 transformants had an amplified fragment with a length shifted from 5.9 kb to 5.2 kb, showing that the same 5 strains were pyrG deletion one wherein pyrG within Asku70 had been replaced by ptrA. The transformant according to the present invention was named *Aspergillus sojae* ASKUPTR8 strain (FIG. 5). No remarkable phenotypes were observed for these strains, and there was no difference in growth rate and reduction of spore-attaching property between these strains and their parent strain.

Figure 6:
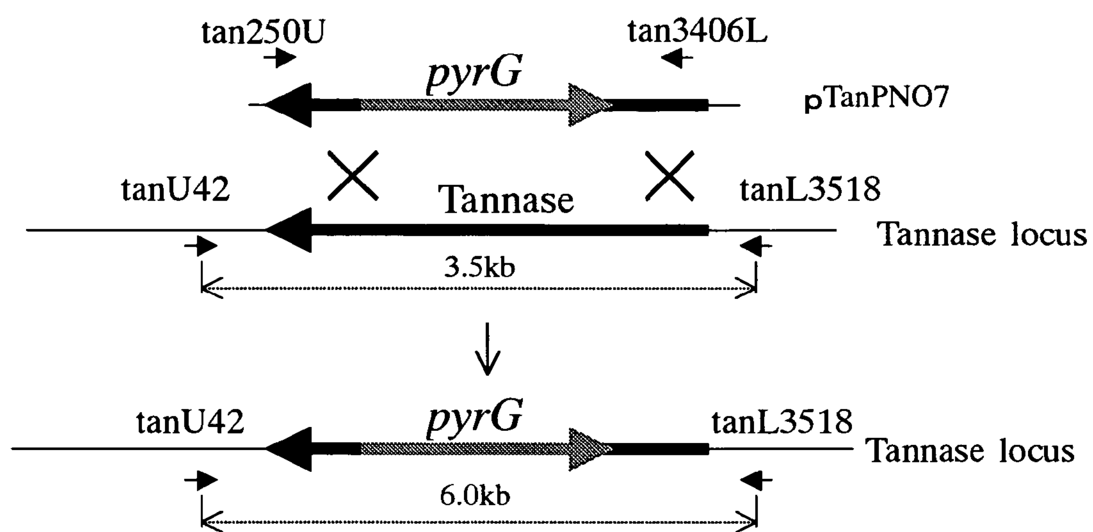
FIG. 6 is a schematic figure showing a process of the production of a tannase gene-disruption strain.
Figure 7:
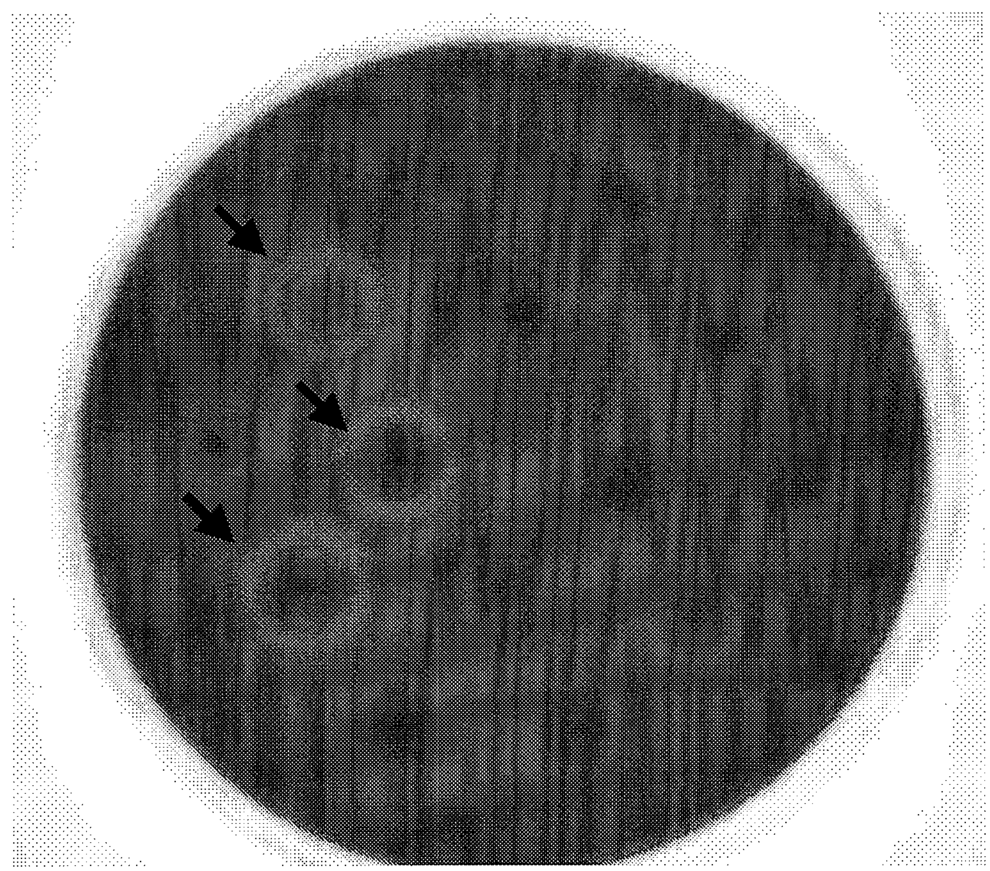
FIG. 7 is a photograph showing the results of screening of the tannase gene-disruption strain by their phenotypes. An arrow shows strains wherein the tannase gene is not disrupted.
Figure 8:
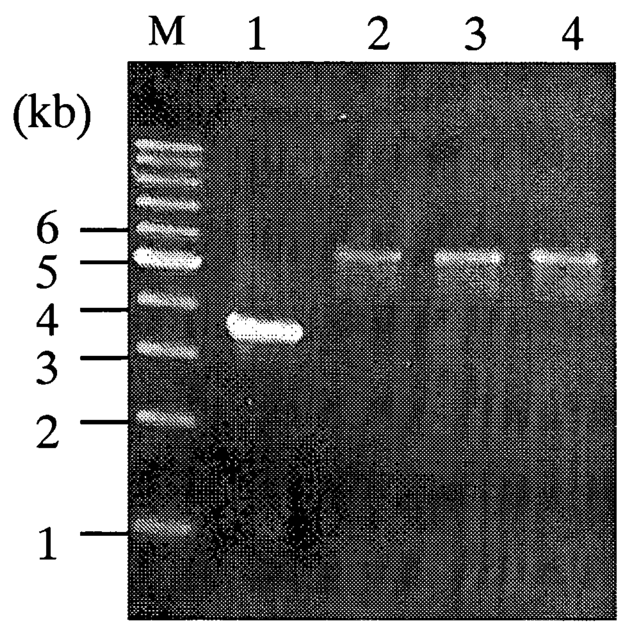
FIG. 8 is a photograph of electrophoresis showing the results of disruption of tannase gene.

Δku70 strain (ASKUPTR8) was then used to obtain a tannase gene-disruption strain by homologous recombination, and the frequency of homologous recombination (gene disruption) was studied. A tannase gene-disruption vector, pTanPNO7 was used (Takahashi et al., 2004 Mol. Gen Genet.). PCR was done using pTanPNO7 as a template and primers tanU250Xb-tanL3406EI to amplify a fragment for gene disruption. *Aspergillus sojae* pyrG deletion strain I-6 and ku70-disruption strain ASKUPTR8 were transformed with the resulting fragment (FIG. 6). A wild-type strain of *Aspergillus sojae* would form halo on a tannic acid plate. On the other hand, as the tannase gene-disruption strain would not from the halo, it could be easily screened (FIG. 7). Accordingly, each resulting transformant was inoculated on the tannic acid plate to observe whether the halo would be formed or not. Most of the transformants derived from the parent I-6 strain formed the halo. Table 1 showed that only 2 tannase gene-disruption strains were obtained among 150 strains with disruption frequency of about 1.3%. On the other hand, 42 transformant strains out of 56 strains derived from the ku70-disruption strain ASKUPTR8 did not form the halo, showing a remarkable increase in disruption frequency up to 75% (Table 1A). Furthermore, the disruption of the tannase gene was confirmed by a shift in the length of a fragment from 3.5 kb to 6.0 kb, which was obtained by amplification using the genomic DNA of the transformant as a template and primers tanU42-tanL3518 (FIG. 8). An arm length of homologous region in the above homologous recombination was 1.4 kb.

Example 2

Figure 9:
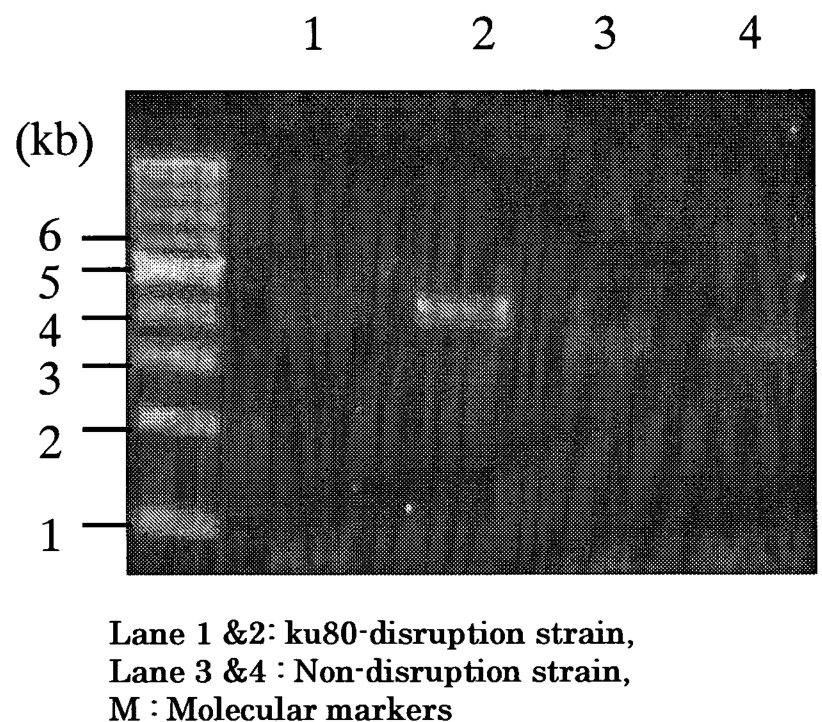
FIG. 9 is a photograph of electrophoresis showing the results of disruption of ku80.

The frequency of gene disruption with respect to the ku80 gene was then examined using the Δ ku70 strain. PCR was done using the ku80-disruption vector pku80pol (FIG. 3) as a template and primers ku2U936Xb-ku2L4698K to amplify a fragment for gene disruption. *Aspergillus sojae* pyrG deletion strain I-6 and the ku70-disruption strain ASKUPTR8 were transformed with the resulting fragment. PCR was done using the genomic DNA extracted from the transformant as a template and primers ku2U830-ku2L4937. As a 3.5 kb band in the parent strain shifted to 4.0 kb band in the gene-disruption strain, the disruption strain could be easily identified (FIG. 9). It was confirmed that the ku80 gene was disrupted in only one strain out of 42 I-6 strains with disruption frequency of 2.4%, and in 18 strains out of 25 ku70-disruption (ASKUPTR8) strains with an increased disruption frequency of 72% (Table 1C). An arm length of homologous region in the above homologous recombination was 1.0 kb.

Example 3

A ku70 antisense RNA-expressing strain was prepared and its effect on the frequency of homologous recombination was examined.

Thus, the ku70 antisense RNA-expressing vector, pRkuA1 in a circular state was introduced into *Aspergillus sojae* pyrG deletion strain I-6 to obtain the transformants (kuA1, kuA2, kuA3 and kuA4) according to the present invention. Selection of the transformants was done with prythiamine. The introduction of the construct for expressing the ku70 antisense RNA was confirmed by PCR and Southern hybridization. Disruption experiment of areA's C-end was carried out using these four strains and a vector arePXB (Takahashi et al., 2004). The four strains were transformed with arePXB vector cut with NotI-Xho, and resulting transformants were transferred to KCIO3-mono-methylammonium (100 mM)-CZ medium. The number of the strains with suppression of growth was counted. As a result, while the disruption of areA's C-end was observed at a ratio of about 0 or 0.7% in the transformants derived from the parent I-6 strain, the same disruption was observed at ratio of about 12.5% and 8% in the kuA1, kuA3 and kuA4 strains showing an increase by 10 times or more (Table 1B). An arm length of homologous region in the above homologous recombination was 0.9 kb.

Disruption experiment of tannase was carried out using these four strains and the vector pTanPNO7 (Takahashi et al., 2004). A wild-type strain of *Aspergillus sojae* would form halo on the tannic acid plate. On the other hand, as the tannase gene-disruption strain would not form the halo, it could be easily screened. As a result, while the disruption of tannase was observed at a ratio of about 1% in the transformants derived from the parent I-6 strain, the same disruption was observed at ratio of about 16% and 12% in the kuA1 and kuA4 strains, respectively, showing an increase by 10 times or more (Table 1A).

Example 4

The effect of ku70-disruption in *Aspergillus oryzae* on the frequency of tannase-disruption was examined.

Figure 10:
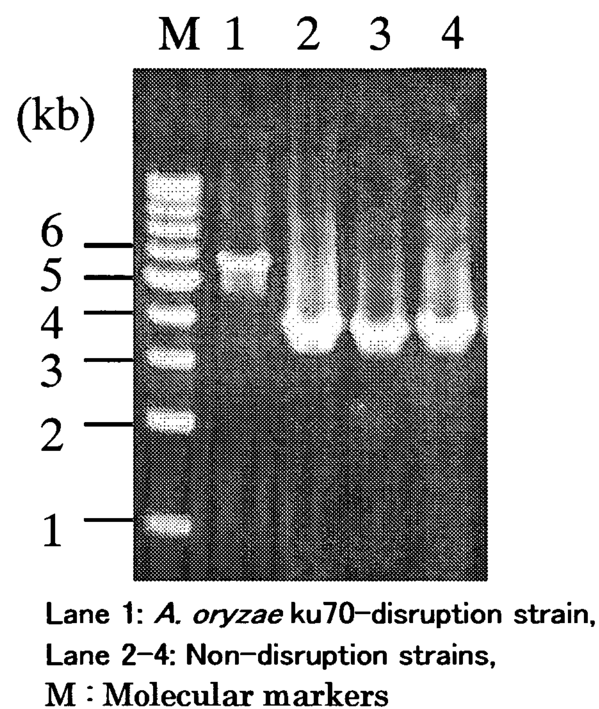
FIG. 10 is a photograph of electrophoresis showing the results of disruption of ku70 of *Aspergillus oryzae*.

Thus, protoplast prepared from and *Aspergillus oryzae* RIB40 pyrG deletion strain was transformed in a conventional method with a DNA fragment amplified by PCR using the ku70-disruption vector pkupyr1 as a template, and primers ku78U and ku3482L. Genomic DNA was obtained from the transformant regenerated on 1.2M sorbitol CZ medium, and subjected to PCR using primers kuU459-kuL4222. As a result, out of 30 transformants was obtained three ku gene-disruption strains that had an amplified fragment with a length shifted from 3.4 kb to 5.9 kb (FIG. 10). The resulting three strains were then transformed in a conventional way with a fragment obtained by amplification of the vector pkuptrH wherein 2.7 Kb BglII fragment containing pyrG had been replaced by ptrA with use of primers ku78U-3482L. After the resulting transformants were transferred to 2 mg/ml-5FOA-CZ, 5FOA-resistant strains were selected. Genomic DNA was extracted from the selected strains and subjected to PCR using primers kuU459-kuL4222. As a result, it was confirmed that 4 strains out of 6 transformants had an amplified fragment with a length shifted from 5.9 kb to 5.2 kb, showing that the same 4 strains were pyrG deletion one wherein pyrG within Asku70 had been replaced by ptrA. The transformant according to the present invention was named *Aspergillus oryzae* strain RkuN16ptr1.

In order to study the frequency of tannase gene-disruption, a fragment for gene disruption was prepared by PCR using pTanPNO7 (Takahashi et al., 2004 Mol. Gen Genet.) as a template and primers tanU250Xb-tanL3406EI. *Aspergillus orzae* ku70-disruption strain RkuN16ptr1 was transformed with the resulting fragment. The resulting 22 transformants were inoculated on the tannic acid plate to observe whether the halo would be formed or not. As a result, 14 transformant strains out of the above 22 strains did not form the halo, showing a remarkable increase in disruption frequency up to 63.4% (Table 1A).

Example 5

The effect of an arm length in a homologous region on the targeting frequency was examined using the tannase gene locus as a target.

Thus, fragments having the arm length of 500 bp, 100 bp and 50 bp were amplified by PCR using the tannase-disruption vector as a template and primers tanU889-tanL2473, tanU1350-tanL2134, and tanU1379-tanL1986, respectively, and used for transformation of the ku70-disruption strain (ASKUPTR8). The results in Table 2 show that each targeting frequency were 14.3%, 0% and 0% in the targeting with use of the fragments with the arm length of 500 bp, 100 bp and 50 bp, respectively. These results demonstrate a positive correlation between the arm length in a homologous region and the frequency of homologous recombination. Accordingly, if the arm length in a homologous region is as short as 100 bp or less, little homologous recombination strain can be obtained. On the other hand, even if the arm length in a homologous region is about 500 bp, the targeting can be performed with a frequency of about 14% (Table 2).

TABLE 1

(A) Disruption of tannase gene

| | Parent Strain | | | | |
|---|---|---|---|---|---|
| | I-6 (ΔpyrG) | kuA1 | kuA4 | ASKUPTR8 | RkuN16ptr1 |
| The Number of Transformant | 150 | 18 | 25 | 56 | 22 |
| The Number of Disruption Strain | 2 | 3 | 3 | 42 | 14 |
| Frequency of Targeting (%) | 1.3 | 16 | 12 | 75 | 63.4 |

I-6: pyrG deletion strain, kuA1 & kuA4: ku70 antisense RNA-expressing strain
ASKUPTR8: *A. sojae* ku70-disruption strain,
RkuN16ptr1: *A. oryzae* ku70-disruption strain (B) Disruption of areA gene

| | Parent Strain | | | | |
|---|---|---|---|---|---|
| | I-6 (ΔpyrG) | I-6 (ΔpyrG) | kuA1 | kuA3 | kuA4 |
| The Number of Transformant | 295 | 24 | 24 | 24 | 24 |
| The Number of Disruption Strain | 2 | 0 | 3 | 2 | 2 |
| Frequency of Targeting (%) | 0.7 | 0 | 12.5 | 8 | 8 |

I-6: pyrG deletion strain, kuA1, kuA3 & kuA4: ku70 antisense RNA-expressing strain, ASKUPTR8: *A. sojae* ku70-disruption strain, (C) Disruption of ku80 gene

| | Parent Strain | |
|---|---|---|
| | I-6 (ΔpyrG) | ASKUPTR8 |
| The Number of Transformant | 42 | 25 |
| The Number of Disruption Strain | 1 | 18 |
| Frequency of Targeting (%) | 2.4 | 72 |

I-6: pyrG deletion strain, ASKUPTR8: *A. sojae* ku70-disruption strain

TABLE 2

| | Parent Strain | | | | |
|---|---|---|---|---|---|
| | I-6 (ΔpyrG) | ASKUPTR8 | | | |
| Arm Length of Homologous Region (bp) | 1400 | 1400 | 500 | 100 | 50 |
| The Number of Transformant | 150 | 56 | 14 | 28 | 35 |
| The Number of Disruption Strain | 2 | 42 | 2 | 0 | 0 |
| Frequency of Targeting (%) | 1.3 | 75 | 14.3 | 0 | 0 |

I-6: pyrG deletion strain, ASKUPTR8: *A. sojae* ku70-disruption strain

TABLE 3

| Primer | Sequence |
|---|---|
| gp365U-K | GGTACCCCAGTACAGTTTCATGCAAAGTTCTA |
| gp1458L-BH | GGATCCTTGGGGGTAGCCATTGTTTAGATGT-GT |
| gpT2855U-S1 | GTCGACGGCCAGTAGGAATCAGGACAGAG |
| gpT3954L-Ps | CTGCAGCCAAGCCTGTCGTCTTGGGCTATTA-CG |
| Ku78U | TTGCACATTTCCTGGCATTGGTATTCGG |
| kuU459 | AAATGCGACAGCACGTCCTCCCTTCC |
| ku714U-S1 | GTCGACGGATGAGTTGGAGCTGAAGCGAATGG |
| ku1764L-BH | GGATCCTAATTGCTGTTAGCAGCGATACTTCA |
| Ku3482L | ACATAGACGAGGACCAAAAGTCCCTACAG |
| kuL4222 | GGCGTTGTTAGAGGGCTTTCGTCCGTTT |
| ku2U830 | CGGTGGCTTTGGTTCGAGAGGTACGA |
| ku2U936Xb | GTGGTCTAGAATGCTCGGCATGTCTGCGGTAT |
| ku2L4698K | ACAGGGTACCCCGTAAAATCGATATTGGAAAG |
| ku2L4937 | AGAGGCAGACGATGGAAGATCAGGACC |
| pyrU204Bg | AGATCTGGTAATGTGCCCCAGGCTTGTCAG |
| pyrL2924Bg | AGATCTTTTCCCACAGGTTGGTGCTAGTC |
| pyrL2939E | GGGGAATTCCGCGGCCTTTACCAAGGTATCG-CGA |
| ptr-Bg2482U | AGATCTCATTGGTAACGAAATGTAAAAGCTA |
| ptr-Bg4443L | AGATCTGGGGTGACGATGAGCCGCTCTTGCATC |
| tanU42 | GGAACCTGGACATTCTCACTCCTCGCGT |
| tanU250Xb | TCTAGACAGCCACGAAGGTTTTGCCTTT |
| tanU889 | TGGATAGCTTTGCACGCGCAAGGGTC |
| tanU1350 | TGCTTTGGCAGCAGGAGCGAACGCAG |
| tanU1379 | CTTTTACCGATGTGTGCACCGTGTCT |
| tanL1986 | GAAAGCCGGGGCACCAGTAATCGCAC |
| tanL2134 | CAACACCGTCGGTTCTTCCATCAAGCGG |
| tanL2473 | GGATGTTGAGCTCCCACTTGCCAGTGTC |
| tanL3406EI | GAATTCTGTTGGTGGGCTTTTGCGTGTGGT |
| tan3518L | CGAGACGGTCCAGGTCCAGGTCTAGGTCTG |

Gene-disruption strains may be very easily produced by using the transformant according to the present invention without accompanying any significant change in phenotypes.

it is therefore conceived that said transformant can be a very strong tool in various genetic analysis such as promoter analysis and modification taking a position-effect into consideration, and expression of a desired gene.

What is claimed is:

1. An *Aspergillus sojae* or *Aspergillus oryzae* transformant having an increased frequency of homologous recombination due to suppression, via disruption or antisense, of an *Aspergillus sojae* or *Aspergillus oryzae* ku70 gene or an *Aspergillus sojae* or *Aspergillus oryzae* ku80 gene, wherein:

the *Aspergillus sojae* ku70 gene comprises the DNA sequence of SEQ. ID. NO: 1 or encodes a protein comprising the sequence of SEQ. ID. NO: 2;

the *Aspergillus sojae* ku80 gene comprises the DNA sequence of SEQ. ID. NO: 3 or encodes a protein comprising the sequence of SEQ. ID. NO: 4;

the *Aspergillus sojae* ku80 gene comprises the DNA sequence of SEQ. ID. NO: 5 or encodes a protein comprising the sequence of SEQ. ID. NO: 6;

the *Aspergillus oryzae* ku70 gene comprises the DNA sequence of SEQ. ID. NO: 7 or encodes a protein comprising the sequence of SEQ. ID. NO: 8;

the *Aspergillus oryzae* ku80 gene comprises the DNA sequence of SEQ. ID. NO: 9 or encodes a protein comprising the sequence of SEQ. ID. NO: 10; or the *Aspergillus oryzae* ku80 gene comprises the DNA sequence of SEQ. ID. NO: 11; or encodes a protein comprising the sequence of SEQ. ID. NO: 12;

wherein the frequency of homologous recombination of the *Aspergillus sojae* or *Aspergillus oryzae* transformant having the ku70 or ku80 gene suppressed via disruption is increased by at least 60 times in comparison to an *Aspergillus sojae* or *Aspergillus oryzae* strain which has not had the ku70 or ku80 gene suppressed, and the frequency of homologous recombination of the *Aspergillus sojae* or *Aspergillus oryzae* transformant having the ku70 or ku80 gene suppressed via antisense is increased by at least 10 times in comparison to an *Aspergillus sojae* or *Aspergillus oryzae* strain which has not had the ku70 or ku80 gene suppressed.

2. The transformant according to claim 1 wherein the ku70 or ku80 gene is disrupted.

3. The transformant according to claim 1, wherein the ku70 or ku80 gene is inactivated by an antisense RNA.

4. The transformant of claim 1, wherein the *Aspergillus oryzae* ku70 gene comprises the sequence of SEQ ID NO: 7.

* * * * *

```
                              SEQUENCE LISTING


<160> NUMBER OF SEQ ID NOS: 41

<210> SEQ ID NO 1
<211> LENGTH: 2249
<212> TYPE: DNA
<213> ORGANISM: Aspergillus sojae
<220> FEATURE:
<221> NAME/KEY: misc_feature
<223> OTHER INFORMATION: Aspergillus sojae Ku70
<220> FEATURE:
<221> NAME/KEY: CDS
<222> LOCATION: (1)..(69)
<220> FEATURE:
<221> NAME/KEY: CDS
<222> LOCATION: (130)..(741)
<220> FEATURE:
<221> NAME/KEY: CDS
<222> LOCATION: (791)..(1637)
<223> OTHER INFORMATION: split codon
<220> FEATURE:
<221> NAME/KEY: CDS
<222> LOCATION: (1696)..(1799)
<223> OTHER INFORMATION: split codon
<220> FEATURE:
<221> NAME/KEY: CDS
<222> LOCATION: (1851)..(2078)
<220> FEATURE:
<221> NAME/KEY: CDS
<222> LOCATION: (2142)..(2246)

<400> SEQUENCE: 1

atg gct gac gag gat caa tat cgc gga gac gac cag atc gat gag gaa       48
Met Ala Asp Glu Asp Gln Tyr Arg Gly Asp Asp Gln Ile Asp Glu Glu
1               5                   10                  15

gag gag gag atc gac gag agt gtacacactt tcaaacacac ctgaaagctt          99
Glu Glu Glu Ile Asp Glu Ser
            20

cggaggctaa catgttatca accaaaatag gga tac aaa aca gtg aaa gat gcc     153
                                 Gly Tyr Lys Thr Val Lys Asp Ala
                                     25                  30

gtt ctt ttt gct atc gaa gtc agc gat tcg atg ctc acc cct cgt cca      201
Val Leu Phe Ala Ile Glu Val Ser Asp Ser Met Leu Thr Pro Arg Pro
            35                  40                  45

tct tcc gat tca aag aaa cct gcg gag gag tcc ccc aca acg gcg gca      249
Ser Ser Asp Ser Lys Lys Pro Ala Glu Glu Ser Pro Thr Thr Ala Ala
        50                  55                  60

cta aaa tgc gca tat cat ctc atg caa caa cgc att atc tct aat ccc      297
Leu Lys Cys Ala Tyr His Leu Met Gln Gln Arg Ile Ile Ser Asn Pro
    65                  70                  75

cgt gac atg atc ggt gtg cta tta tat ggg acg cag gcg tcc aaa ttt      345
Arg Asp Met Ile Gly Val Leu Leu Tyr Gly Thr Gln Ala Ser Lys Phe
80                  85                  90                  95

tat gac gag gat gaa aac agt cga gga gac ctt tca tac cca cac tgc      393
Tyr Asp Glu Asp Glu Asn Ser Arg Gly Asp Leu Ser Tyr Pro His Cys
                100                 105                 110

tac ctg ttc aca gac ctg gat gtt ccc tct gcg caa gaa gtc aag aat      441
Tyr Leu Phe Thr Asp Leu Asp Val Pro Ser Ala Gln Glu Val Lys Asn
            115                 120                 125

ctt cgg gca ctg gca caa gac ggc gat gaa tca gag gat gta ctt aag      489
Leu Arg Ala Leu Ala Gln Asp Gly Asp Glu Ser Glu Asp Val Leu Lys
        130                 135                 140

gcg tca ggc gag cgg gtc tca atg gcg aac gta ctc ttt tgc gcc aat      537
Ala Ser Gly Glu Arg Val Ser Met Ala Asn Val Leu Phe Cys Ala Asn
```

```
    145                 150                 155

caa ata ttc acg tca aaa gcc ccc aac ttc ttg tct cgg cga ttg ttc      585
Gln Ile Phe Thr Ser Lys Ala Pro Asn Phe Leu Ser Arg Arg Leu Phe
160                 165                 170                 175

ata gtc acc gat aat gat gac cct cat ggc gat aac aaa agc ttg aga      633
Ile Val Thr Asp Asn Asp Asp Pro His Gly Asp Asn Lys Ser Leu Arg
                180                 185                 190

tcc gct gca act gta cgc gcg aag gac tta tac gac ctc ggt gtc act      681
Ser Ala Ala Thr Val Arg Ala Lys Asp Leu Tyr Asp Leu Gly Val Thr
            195                 200                 205

att gag ctg ttt ccg att tct cgg cca gac cat gag ttc gat acc gcc      729
Ile Glu Leu Phe Pro Ile Ser Arg Pro Asp His Glu Phe Asp Thr Ala
        210                 215                 220

agg ttc tat gac gtaagattat attgactcaa tgtgaagtat cgctgctaac          781
Arg Phe Tyr Asp
    225

agcaattag gat atc atc tac aag gcc tct cct tcg gat cca gat gcc cca    832
          Asp Ile Ile Tyr Lys Ala Ser Pro Ser Asp Pro Asp Ala Pro
                  230                 235                 240

gcg tac ctg caa act gat tcc aag gct tct cca gct acc ggg gat ggg      880
Ala Tyr Leu Gln Thr Asp Ser Lys Ala Ser Pro Ala Thr Gly Asp Gly
            245                 250                 255

ata tca ctg ctc agt acc ctc ctg tcc agt atc aat tcg aga tct gtc      928
Ile Ser Leu Leu Ser Thr Leu Leu Ser Ser Ile Asn Ser Arg Ser Val
        260                 265                 270

cca cgg cgt gcg cag ttc tcc aac ata cca ttg gag ctg gga cca aac      976
Pro Arg Arg Ala Gln Phe Ser Asn Ile Pro Leu Glu Leu Gly Pro Asn
    275                 280                 285

ttc aaa ata tct gtc tcg gga tat ctt ttg ttc aag cgt caa gca cct     1024
Phe Lys Ile Ser Val Ser Gly Tyr Leu Leu Phe Lys Arg Gln Ala Pro
290                 295                 300                 305

gcc aga aac tcc ttc atc tgg ctc ggc ggt gaa cag ccc cag att gtc     1072
Ala Arg Asn Ser Phe Ile Trp Leu Gly Gly Glu Gln Pro Gln Ile Val
                310                 315                 320

aaa gga gtg acc act caa atc gct gac gac acg gct cgc acg att gag     1120
Lys Gly Val Thr Thr Gln Ile Ala Asp Asp Thr Ala Arg Thr Ile Glu
            325                 330                 335

aag tgg gaa atc aag aaa gct tat aag ttt ggg ggt gat cag gtt gct     1168
Lys Trp Glu Ile Lys Lys Ala Tyr Lys Phe Gly Gly Asp Gln Val Ala
        340                 345                 350

ttc acg ccc gaa gag atg aag tca ctg agg aac ttc ggt gat cct gtc     1216
Phe Thr Pro Glu Glu Met Lys Ser Leu Arg Asn Phe Gly Asp Pro Val
    355                 360                 365

atc cgt ata att ggg ttc aag ccc ctt tct gca ctt ccg ttc tgg gcc     1264
Ile Arg Ile Ile Gly Phe Lys Pro Leu Ser Ala Leu Pro Phe Trp Ala
370                 375                 380                 385

aat atc aaa cac cct tcc ttc ata tac cca tcg gaa gaa gat ttc gtg     1312
Asn Ile Lys His Pro Ser Phe Ile Tyr Pro Ser Glu Glu Asp Phe Val
                390                 395                 400

ggc tcc acg cga gtc ttt tct gct ttg cat cag aca ctt ctc cgg gat     1360
Gly Ser Thr Arg Val Phe Ser Ala Leu His Gln Thr Leu Leu Arg Asp
            405                 410                 415

aaa aag gcc gca ctt gtc tgg ttc att gcg cgt aaa aac gca agc cct     1408
Lys Lys Ala Ala Leu Val Trp Phe Ile Ala Arg Lys Asn Ala Ser Pro
        420                 425                 430

gtt ctg ggg gct atg gtc gct ggc gaa gag aaa cta gac gag agt ggc     1456
Val Leu Gly Ala Met Val Ala Gly Glu Glu Lys Leu Asp Glu Ser Gly
    435                 440                 445

gtc cag aag ttt cct cca gga atg tgg ata ata cct ctc ccg ttc gct     1504
Val Gln Lys Phe Pro Pro Gly Met Trp Ile Ile Pro Leu Pro Phe Ala
```

```
450                 455                 460                 465

gat gac gtc cgt caa aac cct gaa acc aca ctc cat gtt gca ccc gag      1552
Asp Asp Val Arg Gln Asn Pro Glu Thr Thr Leu His Val Ala Pro Glu
                470                 475                 480

cca ttg atc gat caa atg cgg tat att gtt cag caa ctg caa ctt cca      1600
Pro Leu Ile Asp Gln Met Arg Tyr Ile Val Gln Gln Leu Gln Leu Pro
            485                 490                 495

aag gcg tct tac gac ccc ttc aag tac cct aat cca t gtaagcttct         1647
Lys Ala Ser Tyr Asp Pro Phe Lys Tyr Pro Asn Pro
        500                 505

gccaacttcc tgcacagaaa ctctggcatt aacctattgc tctgttag cc  ctc caa     1703
                                                     Ser Leu Gln

tgg cat tat cgc att cta caa gcc tta gcg tta gat gag gac ctc ccg      1751
Trp His Tyr Arg Ile Leu Gln Ala Leu Ala Leu Asp Glu Asp Leu Pro
        515                 520                 525

gag aag cca gaa gac aaa acg ttg ccc aga tat cgg cag att gat aaa      1799
Glu Lys Pro Glu Asp Lys Thr Leu Pro Arg Tyr Arg Gln Ile Asp Lys
    530                 535                 540

gtatatcaca cattcctatt ctttccacgg atcttgctga ccttcgctta g cgc act     1856
                                                         Arg Thr
                                                         545

ggc gac tat gta ttg tct tgg gcc gac gag ttg gaa aag caa tac gcg      1904
Gly Asp Tyr Val Leu Ser Trp Ala Asp Glu Leu Glu Lys Gln Tyr Ala
            550                 555                 560

aaa ata tcg gca cat ggc ccg aag agc aca ctc gtc gaa cga agc gcc      1952
Lys Ile Ser Ala His Gly Pro Lys Ser Thr Leu Val Glu Arg Ser Ala
        565                 570                 575

aaa gac cga aca tct gaa gtt gag gat gca gcc ccg aag cca tac aag      2000
Lys Asp Arg Thr Ser Glu Val Glu Asp Ala Ala Pro Lys Pro Tyr Lys
    580                 585                 590

aaa gtg aag gtg gag aca gac gag caa ggt gtt gaa gat gta gtg cga      2048
Lys Val Lys Val Glu Thr Asp Glu Gln Gly Val Glu Asp Val Val Arg
595                 600                 605                 610

gcc cct tac caa aag gga tcg cta tcg aag gtgactatta cctgcccccct       2098
Ala Pro Tyr Gln Lys Gly Ser Leu Ser Lys
                615                 620

aggctttaat ttggactaac taacgcgcgt gacttgtgtg tag ctt act gta ccc      2153
                                                Leu Thr Val Pro

gtc ctc aaa aac ttc ctg aaa gcc cat gga cgc tcc gct gct ggg aag      2201
Val Leu Lys Asn Phe Leu Lys Ala His Gly Arg Ser Ala Ala Gly Lys
625                 630                 635                 640

aaa aaa gaa ctc gtt gag cgt gtg gag gag tac ctg gag cag aag tga      2249
Lys Lys Glu Leu Val Glu Arg Val Glu Glu Tyr Leu Glu Gln Lys
                645                 650                 655


<210> SEQ ID NO 2
<211> LENGTH: 655
<212> TYPE: PRT
<213> ORGANISM: Aspergillus sojae

<400> SEQUENCE: 2

Met Ala Asp Glu Asp Gln Tyr Arg Gly Asp Asp Gln Ile Asp Glu Glu
1               5                   10                  15

Glu Glu Glu Ile Asp Glu Ser Gly Tyr Lys Thr Val Lys Asp Ala Val
            20                  25                  30

Leu Phe Ala Ile Glu Val Ser Asp Ser Met Leu Thr Pro Arg Pro Ser
        35                  40                  45

Ser Asp Ser Lys Lys Pro Ala Glu Glu Ser Pro Thr Thr Ala Ala Leu
    50                  55                  60
```

-continued

```
Lys Cys Ala Tyr His Leu Met Gln Gln Arg Ile Ile Ser Asn Pro Arg
65                  70                  75                  80

Asp Met Ile Gly Val Leu Leu Tyr Gly Thr Gln Ala Ser Lys Phe Tyr
                85                  90                  95

Asp Glu Asp Glu Asn Ser Arg Gly Asp Leu Ser Tyr Pro His Cys Tyr
            100                 105                 110

Leu Phe Thr Asp Leu Asp Val Pro Ser Ala Gln Glu Val Lys Asn Leu
        115                 120                 125

Arg Ala Leu Ala Gln Asp Gly Asp Glu Ser Glu Asp Val Leu Lys Ala
    130                 135                 140

Ser Gly Glu Arg Val Ser Met Ala Asn Val Leu Phe Cys Ala Asn Gln
145                 150                 155                 160

Ile Phe Thr Ser Lys Ala Pro Asn Phe Leu Ser Arg Arg Leu Phe Ile
                165                 170                 175

Val Thr Asp Asn Asp Asp Pro His Gly Asp Asn Lys Ser Leu Arg Ser
            180                 185                 190

Ala Ala Thr Val Arg Ala Lys Asp Leu Tyr Asp Leu Gly Val Thr Ile
        195                 200                 205

Glu Leu Phe Pro Ile Ser Arg Pro Asp His Glu Phe Asp Thr Ala Arg
    210                 215                 220

Phe Tyr Asp Asp Ile Ile Tyr Lys Ala Ser Pro Ser Asp Pro Asp Ala
225                 230                 235                 240

Pro Ala Tyr Leu Gln Thr Asp Ser Lys Ala Ser Pro Ala Thr Gly Asp
                245                 250                 255

Gly Ile Ser Leu Leu Ser Thr Leu Leu Ser Ser Ile Asn Ser Arg Ser
            260                 265                 270

Val Pro Arg Arg Ala Gln Phe Ser Asn Ile Pro Leu Glu Leu Gly Pro
        275                 280                 285

Asn Phe Lys Ile Ser Val Ser Gly Tyr Leu Leu Phe Lys Arg Gln Ala
    290                 295                 300

Pro Ala Arg Asn Ser Phe Ile Trp Leu Gly Gly Glu Gln Pro Gln Ile
305                 310                 315                 320

Val Lys Gly Val Thr Thr Gln Ile Ala Asp Asp Thr Ala Arg Thr Ile
                325                 330                 335

Glu Lys Trp Glu Ile Lys Lys Ala Tyr Lys Phe Gly Gly Asp Gln Val
            340                 345                 350

Ala Phe Thr Pro Glu Glu Met Lys Ser Leu Arg Asn Phe Gly Asp Pro
        355                 360                 365

Val Ile Arg Ile Ile Gly Phe Lys Pro Leu Ser Ala Leu Pro Phe Trp
    370                 375                 380

Ala Asn Ile Lys His Pro Ser Phe Ile Tyr Pro Ser Glu Glu Asp Phe
385                 390                 395                 400

Val Gly Ser Thr Arg Val Phe Ser Ala Leu His Gln Thr Leu Leu Arg
                405                 410                 415

Asp Lys Lys Ala Ala Leu Val Trp Phe Ile Ala Arg Lys Asn Ala Ser
            420                 425                 430

Pro Val Leu Gly Ala Met Val Ala Gly Glu Glu Lys Leu Asp Glu Ser
        435                 440                 445

Gly Val Gln Lys Phe Pro Pro Gly Met Trp Ile Ile Pro Leu Pro Phe
    450                 455                 460

Ala Asp Asp Val Arg Gln Asn Pro Glu Thr Thr Leu His Val Ala Pro
465                 470                 475                 480

Glu Pro Leu Ile Asp Gln Met Arg Tyr Ile Val Gln Gln Leu Gln Leu
                485                 490                 495
```

```
Pro Lys Ala Ser Tyr Asp Pro Phe Lys Tyr Pro Asn Pro Ser Leu Gln
            500                 505                 510

Trp His Tyr Arg Ile Leu Gln Ala Leu Ala Leu Asp Glu Asp Leu Pro
        515                 520                 525

Glu Lys Pro Glu Asp Lys Thr Leu Pro Arg Tyr Arg Gln Ile Asp Lys
    530                 535                 540

Arg Thr Gly Asp Tyr Val Leu Ser Trp Ala Asp Glu Leu Glu Lys Gln
545                 550                 555                 560

Tyr Ala Lys Ile Ser Ala His Gly Pro Lys Ser Thr Leu Val Glu Arg
                565                 570                 575

Ser Ala Lys Asp Arg Thr Ser Glu Val Glu Asp Ala Ala Pro Lys Pro
            580                 585                 590

Tyr Lys Lys Val Lys Val Glu Thr Asp Glu Gln Gly Val Glu Asp Val
        595                 600                 605

Val Arg Ala Pro Tyr Gln Lys Gly Ser Leu Ser Lys Leu Thr Val Pro
    610                 615                 620

Val Leu Lys Asn Phe Leu Lys Ala His Gly Arg Ser Ala Ala Gly Lys
625                 630                 635                 640

Lys Lys Glu Leu Val Glu Arg Val Glu Glu Tyr Leu Glu Gln Lys
                645                 650                 655


<210> SEQ ID NO 3
<211> LENGTH: 2707
<212> TYPE: DNA
<213> ORGANISM: Aspergillus sojae
<220> FEATURE:
<221> NAME/KEY: misc_feature
<223> OTHER INFORMATION: Aspergillus sojae Ku80 Long
<220> FEATURE:
<221> NAME/KEY: CDS
<222> LOCATION: (1)..(129)
<220> FEATURE:
<221> NAME/KEY: CDS
<222> LOCATION: (192)..(246)
<223> OTHER INFORMATION: split codon
<220> FEATURE:
<221> NAME/KEY: CDS
<222> LOCATION: (302)..(368)
<223> OTHER INFORMATION: split codon
<220> FEATURE:
<221> NAME/KEY: CDS
<222> LOCATION: (427)..(494)
<223> OTHER INFORMATION: split codon
<220> FEATURE:
<221> NAME/KEY: CDS
<222> LOCATION: (553)..(721)
<223> OTHER INFORMATION: split codon
<220> FEATURE:
<221> NAME/KEY: CDS
<222> LOCATION: (774)..(834)
<223> OTHER INFORMATION: split codon
<220> FEATURE:
<221> NAME/KEY: CDS
<222> LOCATION: (884)..(1420)
<223> OTHER INFORMATION: split codon
<220> FEATURE:
<221> NAME/KEY: CDS
<222> LOCATION: (1473)..(1858)
<223> OTHER INFORMATION: split codon
<220> FEATURE:
<221> NAME/KEY: CDS
<222> LOCATION: (1909)..(2120)
<223> OTHER INFORMATION: split codon
<220> FEATURE:
<221> NAME/KEY: CDS
<222> LOCATION: (2173)..(2639)
<223> OTHER INFORMATION: split codon
<220> FEATURE:
<221> NAME/KEY: CDS
```

```
<222> LOCATION: (2690)..(2704)

<400> SEQUENCE: 3

atg gcg gac aag gaa gca act gtg tat att gtg gac gtt ggg agg tcc       48
Met Ala Asp Lys Glu Ala Thr Val Tyr Ile Val Asp Val Gly Arg Ser
1               5                   10                  15

atg gga gaa tgt cgc aat ggc cga tca gtg act gat ctt gaa tgg gcc       96
Met Gly Glu Cys Arg Asn Gly Arg Ser Val Thr Asp Leu Glu Trp Ala
            20                  25                  30

atg cag tat gtc tgg gat cgc att aca gga aca gtgagtggca gtcgtcacaa    149
Met Gln Tyr Val Trp Asp Arg Ile Thr Gly Thr
        35                  40

ttgggctgca ttcgttaaat atcttgctca atttcagacc ag gtg gcc act ggc       203
                                               Val Ala Thr Gly
                                                   45

cgt aaa act gcc acg atg ggt gtg atc gga ctc agg aca gat g            246
Arg Lys Thr Ala Thr Met Gly Val Ile Gly Leu Arg Thr Asp
        50                  55                  60

gtatgtatac ttctgaatac tgtatgcggt tcatacactg aaccaaaaaa attag aa      303
                                                              Glu

acg tcc aac gaa ctt gaa gat gac gta cat ttc tct cac att gca gtt      351
Thr Ser Asn Glu Leu Glu Asp Asp Val His Phe Ser His Ile Ala Val
        65                  70                  75

ctg tcg aac atc aaa ca  gtatgctttc cactctatga taatttggtt             398
Leu Ser Asn Ile Lys Gln
    80

cgtgcgccaa actgacgagg acgtcaag g ttt ctt atg ccg gac att cgg aaa     451
                                 Phe Leu Met Pro Asp Ile Arg Lys
                                 85                  90

ctg gaa gat gaa ttg aaa ccg agc aaa acg gac aag gga gac g            494
Leu Glu Asp Glu Leu Lys Pro Ser Lys Thr Asp Lys Gly Asp
        95                  100                 105

gtaagttttt tgtaagccac taggacctac tgtccactta ctaaacttca ttctctag      552

ct  att tcc gct att atc ttg gct att cag atg att atc acg cat tgc      599
Ala Ile Ser Ala Ile Ile Leu Ala Ile Gln Met Ile Ile Thr His Cys
            110                 115                 120

aag aag ttg aag tac agg cgc aag atc gcc cta gtc act aac gga cag      647
Lys Lys Leu Lys Tyr Arg Arg Lys Ile Ala Leu Val Thr Asn Gly Gln
        125                 130                 135

ggg cgc atg agt gat gag gac ctg ggc gag att gtg aaa aag gtc aag      695
Gly Arg Met Ser Asp Glu Asp Leu Gly Glu Ile Val Lys Lys Val Lys
    140                 145                 150

gaa gat aac atc gag ctt gtt gtt at  gtcagtgatt tgctacaaga            741
Glu Asp Asn Ile Glu Leu Val Val Met
155                 160

tagcaacgaa acaaaaagct aacgtcaagc ag g gga att gat ttc gat gac cct    795
                                      Gly Ile Asp Phe Asp Asp Pro
                                          165                 170

gag tac ggt tac aaa gaa gaa gac aaa gac cct cgc aag gtagcgatat       844
Glu Tyr Gly Tyr Lys Glu Glu Asp Lys Asp Pro Arg Lys
                175                 180

ctcttgcgca gctttattcg tatctaataa ctaaaacag gcc gaa aac gaa act       898
                                           Ala Glu Asn Glu Thr
                                               185

ctc ttg cgt acc ctc gtg gaa gat tgt gat gga gtt tat gga aca ttc      946
Leu Leu Arg Thr Leu Val Glu Asp Cys Asp Gly Val Tyr Gly Thr Phe
    190                 195                 200

gag cag gct gtg gct gaa cta gac att ccc cgt gtc aag tct gtc agg      994
Glu Gln Ala Val Ala Glu Leu Asp Ile Pro Arg Val Lys Ser Val Arg
205                 210                 215                 220
```

-continued

```
tca gtg gca agc ttt aaa gga tat ctc caa cta ggc aac cca gag gat     1042
Ser Val Ala Ser Phe Lys Gly Tyr Leu Gln Leu Gly Asn Pro Glu Asp
                225                 230                 235

tat gac tct gct ctc cgc att cct gtt gaa agg tac tac cgg act tac     1090
Tyr Asp Ser Ala Leu Arg Ile Pro Val Glu Arg Tyr Tyr Arg Thr Tyr
            240                 245                 250

ccg gcc aaa ccc cca acc gca agt tct ttc gtc ctg cgc tca gag cct     1138
Pro Ala Lys Pro Pro Thr Ala Ser Ser Phe Val Leu Arg Ser Glu Pro
        255                 260                 265

gaa gct gga caa gaa gag gca gag tca tct gag gct gct gct gct aca     1186
Glu Ala Gly Gln Glu Glu Ala Glu Ser Ser Glu Ala Ala Ala Ala Thr
    270                 275                 280

caa aaa ggg agc cag tct gga gat atc gga ctc act act gtg aga acc     1234
Gln Lys Gly Ser Gln Ser Gly Asp Ile Gly Leu Thr Thr Val Arg Thr
285                 290                 295                 300

atg aga aca tat caa gtt gag gac aaa agt gca ccg ggt ggg aaa atc     1282
Met Arg Thr Tyr Gln Val Glu Asp Lys Ser Ala Pro Gly Gly Lys Ile
                305                 310                 315

gac atc gaa cga gat gac ctc gcc aaa gga tat gag tat gga cgg aca     1330
Asp Ile Glu Arg Asp Asp Leu Ala Lys Gly Tyr Glu Tyr Gly Arg Thr
            320                 325                 330

gca gtt cac att agt gaa acc gac gag aac atc acg att ctc gat aca     1378
Ala Val His Ile Ser Glu Thr Asp Glu Asn Ile Thr Ile Leu Asp Thr
        335                 340                 345

ttc gca ggg ctg gag ttg atg ggc ttc atc cag act gac cgg             1420
Phe Ala Gly Leu Glu Leu Met Gly Phe Ile Gln Thr Asp Arg
    350                 355                 360

gtatgtcttg ctgaagtcgc ctcggtgcat gctctgacac gattaattat ag tat caa   1478
                                                          Tyr Gln

cgt tat atg cac atg tcc aac aca aac atc ata att gca caa cgt gcc     1526
Arg Tyr Met His Met Ser Asn Thr Asn Ile Ile Ile Ala Gln Arg Ala
365                 370                 375                 380

aac gac aaa gca gcc ctt gcc ctt tca tcc ttt ata cac gcg ctt ttt     1574
Asn Asp Lys Ala Ala Leu Ala Leu Ser Ser Phe Ile His Ala Leu Phe
                385                 390                 395

gag cta gaa tgc tat gct gtt gct cgc cta gtc gtg aaa gag aac aag     1622
Glu Leu Glu Cys Tyr Ala Val Ala Arg Leu Val Val Lys Glu Asn Lys
            400                 405                 410

cca cct gtt ata gtc ttg ctc gcg ccc tcg atc gag cct gat tat gaa     1670
Pro Pro Val Ile Val Leu Leu Ala Pro Ser Ile Glu Pro Asp Tyr Glu
        415                 420                 425

tgc ctt ctc gaa gtc cag tta cca ttc gcg gaa gat gtc cga acc tat     1718
Cys Leu Leu Glu Val Gln Leu Pro Phe Ala Glu Asp Val Arg Thr Tyr
    430                 435                 440

cgg ttc cct cct ctg gat aaa gtg att act gtt tct gga aag gtt gtg     1766
Arg Phe Pro Pro Leu Asp Lys Val Ile Thr Val Ser Gly Lys Val Val
445                 450                 455                 460

acg caa cac cgg aat ctt ccc aat gat gat tta ctc gat gtg atg ggc     1814
Thr Gln His Arg Asn Leu Pro Asn Asp Asp Leu Leu Asp Val Met Gly
                465                 470                 475

aag tac gtg aat agt atg gag ctt gtc gac gca gat gag gat gg          1858
Lys Tyr Val Asn Ser Met Glu Leu Val Asp Ala Asp Glu Asp Gly
            480                 485                 490

gtaggtttat gcctaaaaga ttccgaatct cttctcattg acaaaaccag g gat cca    1915
                                                         Asp Pro

gtt gag act ttc cct atc gac gac tcg tat tcg cct gtt ttg cac cgg     1963
Val Glu Thr Phe Pro Ile Asp Asp Ser Tyr Ser Pro Val Leu His Arg
    495                 500                 505

att gac gcc gcc atc cgt gct cgg gct ata cac cct gac cag ccc ata     2011
```

-continued

```
Ile Asp Ala Ala Ile Arg Ala Arg Ala Ile His Pro Asp Gln Pro Ile
510                 515                 520                 525

cct cct cca tca gag aga ctg aca aaa ttc tca cac cca cga gag gat     2059
Pro Pro Pro Ser Glu Arg Leu Thr Lys Phe Ser His Pro Arg Glu Asp
                530                 535                 540

ctc atc gag aga tca cag aaa tac cta gag aag ttg atc gag ata gcc     2107
Leu Ile Glu Arg Ser Gln Lys Tyr Leu Glu Lys Leu Ile Glu Ile Ala
            545                 550                 555

gat gtt aag aag g gttggacatc atcccacaat caagtctatc aggctgctaa       2160
Asp Val Lys Lys
        560

ttctgttacc ag tt  cct ccc aaa gcg aag ggt cgt aag cgc act cgc gaa   2210
              Val Pro Pro Lys Ala Lys Gly Arg Lys Arg Thr Arg Glu
                          565                 570

act gag aag ccg ctt tcc gga ctc gac gtc gat gcc ctg ctt cat cat     2258
Thr Glu Lys Pro Leu Ser Gly Leu Asp Val Asp Ala Leu Leu His His
575                 580                 585                 590

gaa aag cgc gcc aag ata tct ccc aac aat gcc att ccc gag ttc aag     2306
Glu Lys Arg Ala Lys Ile Ser Pro Asn Asn Ala Ile Pro Glu Phe Lys
                595                 600                 605

cag act ctc gca cag gcc gag aat atc gag gcc atc aaa gac gct aca     2354
Gln Thr Leu Ala Gln Ala Glu Asn Ile Glu Ala Ile Lys Asp Ala Thr
            610                 615                 620

aag cag atg atg gtt atc gtt gaa gat caa atc aaa cac agt ctc ggt     2402
Lys Gln Met Met Val Ile Val Glu Asp Gln Ile Lys His Ser Leu Gly
        625                 630                 635

gat gct aac tac gac cgg gtc att gaa gcg ctg ggc acg atg cgt gac     2450
Asp Ala Asn Tyr Asp Arg Val Ile Glu Ala Leu Gly Thr Met Arg Asp
    640                 645                 650

gag ttg gta tca tac gaa gag cct acc tcc tac aat aac ttc cta ggc     2498
Glu Leu Val Ser Tyr Glu Glu Pro Thr Ser Tyr Asn Asn Phe Leu Gly
655                 660                 665                 670

cag ctc aag gat aag ttg tta cag gag aag ctt gga gga gat cga caa     2546
Gln Leu Lys Asp Lys Leu Leu Gln Glu Lys Leu Gly Gly Asp Arg Gln
                675                 680                 685

gag ctg tgg tgg ctt att cga cga aac aag ctg gga ctt gtc act cag     2594
Glu Leu Trp Trp Leu Ile Arg Arg Asn Lys Leu Gly Leu Val Thr Gln
            690                 695                 700

cgc gag tcg gat caa tct agg gtt acc gat acg gaa gcc aaa gaa         2639
Arg Glu Ser Asp Gln Ser Arg Val Thr Asp Thr Glu Ala Lys Glu
        705                 710                 715

gtaagtctca ttaagatgaa ggagtgacct agactaaccg cagtttacag ttc atg      2695

Phe Met
tcc gcc aaa tga                                                     2707
Ser Ala Lys
720


<210> SEQ ID NO 4
<211> LENGTH: 722
<212> TYPE: PRT
<213> ORGANISM: Aspergillus sojae

<400> SEQUENCE: 4

Met Ala Asp Lys Glu Ala Thr Val Tyr Ile Val Asp Val Gly Arg Ser
1               5                   10                  15

Met Gly Glu Cys Arg Asn Gly Arg Ser Val Thr Asp Leu Glu Trp Ala
            20                  25                  30

Met Gln Tyr Val Trp Asp Arg Ile Thr Gly Thr Val Ala Thr Gly Arg
        35                  40                  45

Lys Thr Ala Thr Met Gly Val Ile Gly Leu Arg Thr Asp Glu Thr Ser
```

```
    50                  55                  60

Asn Glu Leu Glu Asp Asp Val His Phe Ser His Ile Ala Val Leu Ser
65                  70                  75                  80

Asn Ile Lys Gln Phe Leu Met Pro Asp Ile Arg Lys Leu Glu Asp Glu
                85                  90                  95

Leu Lys Pro Ser Lys Thr Asp Lys Gly Asp Ala Ile Ser Ala Ile Ile
            100                 105                 110

Leu Ala Ile Gln Met Ile Ile Thr His Cys Lys Lys Leu Lys Tyr Arg
        115                 120                 125

Arg Lys Ile Ala Leu Val Thr Asn Gly Gln Gly Arg Met Ser Asp Glu
    130                 135                 140

Asp Leu Gly Glu Ile Val Lys Lys Val Lys Glu Asp Asn Ile Glu Leu
145                 150                 155                 160

Val Val Met Gly Ile Asp Phe Asp Asp Pro Glu Tyr Gly Tyr Lys Glu
                165                 170                 175

Glu Asp Lys Asp Pro Arg Lys Ala Glu Asn Glu Thr Leu Leu Arg Thr
            180                 185                 190

Leu Val Glu Asp Cys Asp Gly Val Tyr Gly Thr Phe Glu Gln Ala Val
        195                 200                 205

Ala Glu Leu Asp Ile Pro Arg Val Lys Ser Val Arg Ser Val Ala Ser
    210                 215                 220

Phe Lys Gly Tyr Leu Gln Leu Gly Asn Pro Glu Asp Tyr Asp Ser Ala
225                 230                 235                 240

Leu Arg Ile Pro Val Glu Arg Tyr Tyr Arg Thr Tyr Pro Ala Lys Pro
                245                 250                 255

Pro Thr Ala Ser Ser Phe Val Leu Arg Ser Glu Pro Glu Ala Gly Gln
            260                 265                 270

Glu Glu Ala Glu Ser Ser Glu Ala Ala Ala Ala Thr Gln Lys Gly Ser
        275                 280                 285

Gln Ser Gly Asp Ile Gly Leu Thr Thr Val Arg Thr Met Arg Thr Tyr
    290                 295                 300

Gln Val Glu Asp Lys Ser Ala Pro Gly Gly Lys Ile Asp Ile Glu Arg
305                 310                 315                 320

Asp Asp Leu Ala Lys Gly Tyr Glu Tyr Gly Arg Thr Ala Val His Ile
                325                 330                 335

Ser Glu Thr Asp Glu Asn Ile Thr Ile Leu Asp Thr Phe Ala Gly Leu
            340                 345                 350

Glu Leu Met Gly Phe Ile Gln Thr Asp Arg Tyr Gln Arg Tyr Met His
        355                 360                 365

Met Ser Asn Thr Asn Ile Ile Ile Ala Gln Arg Ala Asn Asp Lys Ala
    370                 375                 380

Ala Leu Ala Leu Ser Ser Phe Ile His Ala Leu Phe Glu Leu Glu Cys
385                 390                 395                 400

Tyr Ala Val Ala Arg Leu Val Val Lys Glu Asn Lys Pro Pro Val Ile
                405                 410                 415

Val Leu Leu Ala Pro Ser Ile Glu Pro Asp Tyr Glu Cys Leu Leu Glu
            420                 425                 430

Val Gln Leu Pro Phe Ala Glu Asp Val Arg Thr Tyr Arg Phe Pro Pro
        435                 440                 445

Leu Asp Lys Val Ile Thr Val Ser Gly Lys Val Val Thr Gln His Arg
    450                 455                 460

Asn Leu Pro Asn Asp Asp Leu Leu Asp Val Met Gly Lys Tyr Val Asn
465                 470                 475                 480
```

```
Ser Met Glu Leu Val Asp Ala Asp Glu Asp Gly Asp Pro Val Glu Thr
                485                 490                 495

Phe Pro Ile Asp Asp Ser Tyr Ser Pro Val Leu His Arg Ile Asp Ala
            500                 505                 510

Ala Ile Arg Ala Arg Ala Ile His Pro Asp Gln Pro Ile Pro Pro Pro
        515                 520                 525

Ser Glu Arg Leu Thr Lys Phe Ser His Pro Arg Glu Asp Leu Ile Glu
    530                 535                 540

Arg Ser Gln Lys Tyr Leu Glu Lys Leu Ile Glu Ile Ala Asp Val Lys
545                 550                 555                 560

Lys Val Pro Pro Lys Ala Lys Gly Arg Lys Arg Thr Arg Glu Thr Glu
                565                 570                 575

Lys Pro Leu Ser Gly Leu Asp Val Asp Ala Leu Leu His His Glu Lys
            580                 585                 590

Arg Ala Lys Ile Ser Pro Asn Asn Ala Ile Pro Glu Phe Lys Gln Thr
        595                 600                 605

Leu Ala Gln Ala Glu Asn Ile Glu Ala Ile Lys Asp Ala Thr Lys Gln
    610                 615                 620

Met Met Val Ile Val Glu Asp Gln Ile Lys His Ser Leu Gly Asp Ala
625                 630                 635                 640

Asn Tyr Asp Arg Val Ile Glu Ala Leu Gly Thr Met Arg Asp Glu Leu
                645                 650                 655

Val Ser Tyr Glu Glu Pro Thr Ser Tyr Asn Asn Phe Leu Gly Gln Leu
            660                 665                 670

Lys Asp Lys Leu Leu Gln Glu Lys Leu Gly Gly Asp Arg Gln Glu Leu
        675                 680                 685

Trp Trp Leu Ile Arg Arg Asn Lys Leu Gly Leu Val Thr Gln Arg Glu
    690                 695                 700

Ser Asp Gln Ser Arg Val Thr Asp Thr Glu Ala Lys Glu Phe Met Ser
705                 710                 715                 720

Ala Lys
```

<210> SEQ ID NO 5
<211> LENGTH: 2666
<212> TYPE: DNA
<213> ORGANISM: Aspergillus sojae
<220> FEATURE:
<221> NAME/KEY: misc_feature
<223> OTHER INFORMATION: Aspergillus sojae Ku80 Short
<220> FEATURE:
<221> NAME/KEY: CDS
<222> LOCATION: (1)..(129)
<220> FEATURE:
<221> NAME/KEY: CDS
<222> LOCATION: (192)..(246)
<223> OTHER INFORMATION: split codon
<220> FEATURE:
<221> NAME/KEY: CDS
<222> LOCATION: (302)..(368)
<223> OTHER INFORMATION: split codon
<220> FEATURE:
<221> NAME/KEY: CDS
<222> LOCATION: (427)..(494)
<223> OTHER INFORMATION: split codon
<220> FEATURE:
<221> NAME/KEY: CDS
<222> LOCATION: (553)..(721)
<223> OTHER INFORMATION: split codon
<220> FEATURE:
<221> NAME/KEY: CDS
<222> LOCATION: (774)..(834)
<223> OTHER INFORMATION: split codon
<220> FEATURE:
<221> NAME/KEY: CDS

```
<222> LOCATION: (884)..(1420)
<220> FEATURE:
<221> NAME/KEY: CDS
<222> LOCATION: (1473)..(1858)
<223> OTHER INFORMATION: split codon
<220> FEATURE:
<221> NAME/KEY: CDS
<222> LOCATION: (1909)..(2120)
<223> OTHER INFORMATION: split codon
<220> FEATURE:
<221> NAME/KEY: CDS
<222> LOCATION: (2173)..(2663)
<223> OTHER INFORMATION: split codon

<400> SEQUENCE: 5

atg gcg gac aag gaa gca act gtg tat att gtg gac gtt ggg agg tcc       48
Met Ala Asp Lys Glu Ala Thr Val Tyr Ile Val Asp Val Gly Arg Ser
1               5                   10                  15

atg gga gaa tgt cgc aat ggc cga tca gtg act gat ctt gaa tgg gcc       96
Met Gly Glu Cys Arg Asn Gly Arg Ser Val Thr Asp Leu Glu Trp Ala
            20                  25                  30

atg cag tat gtc tgg gat cgc att aca gga aca gtgagtggca gtcgtcacaa    149
Met Gln Tyr Val Trp Asp Arg Ile Thr Gly Thr
        35                  40

ttgggctgca ttcgttaaat atcttgctca atttcagacc ag gtg gcc act ggc       203
                                               Val Ala Thr Gly
                                                   45

cgt aaa act gcc acg atg ggt gtg atc gga ctc agg aca gat g           246
Arg Lys Thr Ala Thr Met Gly Val Ile Gly Leu Arg Thr Asp
        50                  55                  60

gtatgtatac ttctgaatac tgtatgcggt tcatacactg aaccaaaaaa attag aa      303
                                                             Glu

acg tcc aac gaa ctt gaa gat gac gta cat ttc tct cac att gca gtt      351
Thr Ser Asn Glu Leu Glu Asp Asp Val His Phe Ser His Ile Ala Val
        65                  70                  75

ctg tcg aac atc aaa ca  gtatgctttc cactctatga taatttggtt            398
Leu Ser Asn Ile Lys Gln
    80

cgtgcgccaa actgacgagg acgtcaag g ttt ctt atg ccg gac att cgg aaa     451
                                 Phe Leu Met Pro Asp Ile Arg Lys
                                 85                  90

ctg gaa gat gaa ttg aaa ccg agc aaa acg gac aag gga gac g           494
Leu Glu Asp Glu Leu Lys Pro Ser Lys Thr Asp Lys Gly Asp
        95                  100                 105

gtaagttttt tgtaagccac taggacctac tgtccactta ctaaacttca ttctctag      552

ct  att tcc gct att atc ttg gct att cag atg att atc acg cat tgc      599
Ala Ile Ser Ala Ile Ile Leu Ala Ile Gln Met Ile Ile Thr His Cys
            110                 115                 120

aag aag ttg aag tac agg cgc aag atc gcc cta gtc act aac gga cag      647
Lys Lys Leu Lys Tyr Arg Arg Lys Ile Ala Leu Val Thr Asn Gly Gln
        125                 130                 135

ggg cgc atg agt gat gag gac ctg ggc gag att gtg aaa aag gtc aag      695
Gly Arg Met Ser Asp Glu Asp Leu Gly Glu Ile Val Lys Lys Val Lys
    140                 145                 150

gaa gat aac atc gag ctt gtt gtt at  gtcagtgatt tgctacaaga          741
Glu Asp Asn Ile Glu Leu Val Val Met
155                 160

tagcaacgaa acaaaaagct aacgtcaagc ag g gga att gat ttc gat gac cct    795
                                      Gly Ile Asp Phe Asp Asp Pro
                                          165                 170

gag tac ggt tac aaa gaa gaa gac aaa gac cct cgc aag gtagcgatat      844
Glu Tyr Gly Tyr Lys Glu Glu Asp Lys Asp Pro Arg Lys
                175                 180
```

```
ctcttgcgca gctttattcg tatctaataa ctaaaacag gcc gaa aac gaa act       898
                                          Ala Glu Asn Glu Thr
                                              185

ctc ttg cgt acc ctc gtg gaa gat tgt gat gga gtt tat gga aca ttc      946
Leu Leu Arg Thr Leu Val Glu Asp Cys Asp Gly Val Tyr Gly Thr Phe
    190                 195                 200

gag cag gct gtg gct gaa cta gac att ccc cgt gtc aag tct gtc agg      994
Glu Gln Ala Val Ala Glu Leu Asp Ile Pro Arg Val Lys Ser Val Arg
205                 210                 215                 220

tca gtg gca agc ttt aaa gga tat ctc caa cta ggc aac cca gag gat     1042
Ser Val Ala Ser Phe Lys Gly Tyr Leu Gln Leu Gly Asn Pro Glu Asp
                225                 230                 235

tat gac tct gct ctc cgc att cct gtt gaa agg tac tac cgg act tac     1090
Tyr Asp Ser Ala Leu Arg Ile Pro Val Glu Arg Tyr Tyr Arg Thr Tyr
            240                 245                 250

ccg gcc aaa ccc cca acc gca agt tct ttc gtc ctg cgc tca gag cct     1138
Pro Ala Lys Pro Pro Thr Ala Ser Ser Phe Val Leu Arg Ser Glu Pro
        255                 260                 265

gaa gct gga caa gaa gag gca gag tca tct gag gct gct gct gct aca     1186
Glu Ala Gly Gln Glu Glu Ala Glu Ser Ser Glu Ala Ala Ala Ala Thr
    270                 275                 280

caa aaa ggg agc cag tct gga gat atc gga ctc act act gtg aga acc     1234
Gln Lys Gly Ser Gln Ser Gly Asp Ile Gly Leu Thr Thr Val Arg Thr
285                 290                 295                 300

atg aga aca tat caa gtt gag gac aaa agt gca ccg ggt ggg aaa atc     1282
Met Arg Thr Tyr Gln Val Glu Asp Lys Ser Ala Pro Gly Gly Lys Ile
                305                 310                 315

gac atc gaa cga gat gac ctc gcc aaa gga tat gag tat gga cgg aca     1330
Asp Ile Glu Arg Asp Asp Leu Ala Lys Gly Tyr Glu Tyr Gly Arg Thr
            320                 325                 330

gca gtt cac att agt gaa acc gac gag aac atc acg att ctc gat aca     1378
Ala Val His Ile Ser Glu Thr Asp Glu Asn Ile Thr Ile Leu Asp Thr
        335                 340                 345

ttc gca ggg ctg gag ttg atg ggc ttc atc cag act gac cgg             1420
Phe Ala Gly Leu Glu Leu Met Gly Phe Ile Gln Thr Asp Arg
    350                 355                 360

gtatgtcttg ctgaagtcgc ctcggtgcat gctctgacac gattaattat ag tat caa   1478
                                                          Tyr Gln

cgt tat atg cac atg tcc aac aca aac atc ata att gca caa cgt gcc     1526
Arg Tyr Met His Met Ser Asn Thr Asn Ile Ile Ile Ala Gln Arg Ala
365                 370                 375                 380

aac gac aaa gca gcc ctt gcc ctt tca tcc ttt ata cac gcg ctt ttt     1574
Asn Asp Lys Ala Ala Leu Ala Leu Ser Ser Phe Ile His Ala Leu Phe
                385                 390                 395

gag cta gaa tgc tat gct gtt gct cgc cta gtc gtg aaa gag aac aag     1622
Glu Leu Glu Cys Tyr Ala Val Ala Arg Leu Val Val Lys Glu Asn Lys
            400                 405                 410

cca cct gtt ata gtc ttg ctc gcg ccc tcg atc gag cct gat tat gaa     1670
Pro Pro Val Ile Val Leu Leu Ala Pro Ser Ile Glu Pro Asp Tyr Glu
        415                 420                 425

tgc ctt ctc gaa gtc cag tta cca ttc gcg gaa gat gtc cga acc tat     1718
Cys Leu Leu Glu Val Gln Leu Pro Phe Ala Glu Asp Val Arg Thr Tyr
    430                 435                 440

cgg ttc cct cct ctg gat aaa gtg att act gtt tct gga aag gtt gtg     1766
Arg Phe Pro Pro Leu Asp Lys Val Ile Thr Val Ser Gly Lys Val Val
445                 450                 455                 460

acg caa cac cgg aat ctt ccc aat gat gat tta ctc gat gtg atg ggc     1814
Thr Gln His Arg Asn Leu Pro Asn Asp Asp Leu Leu Asp Val Met Gly
                465                 470                 475
```

```
aag tac gtg aat agt atg gag ctt gtc gac gca gat gag gat gg         1858
Lys Tyr Val Asn Ser Met Glu Leu Val Asp Ala Asp Glu Asp Gly
            480                 485                 490

gtaggtttat gcctaaaaga ttccgaatct cttctcattg acaaaaccag g gat cca   1915
                                                         Asp Pro

gtt gag act ttc cct atc gac gac tcg tat tcg cct gtt ttg cac cgg    1963
Val Glu Thr Phe Pro Ile Asp Asp Ser Tyr Ser Pro Val Leu His Arg
    495                 500                 505

att gac gcc gcc atc cgt gct cgg gct ata cac cct gac cag ccc ata    2011
Ile Asp Ala Ala Ile Arg Ala Arg Ala Ile His Pro Asp Gln Pro Ile
510                 515                 520                 525

cct cct cca tca gag aga ctg aca aaa ttc tca cac cca cga gag gat    2059
Pro Pro Pro Ser Glu Arg Leu Thr Lys Phe Ser His Pro Arg Glu Asp
                530                 535                 540

ctc atc gag aga tca cag aaa tac cta gag aag ttg atc gag ata gcc    2107
Leu Ile Glu Arg Ser Gln Lys Tyr Leu Glu Lys Leu Ile Glu Ile Ala
            545                 550                 555

gat gtt aag aag g gttggacatc atcccacaat caagtctatc aggctgctaa      2160
Asp Val Lys Lys
        560

ttctgttacc ag tt  cct ccc aaa gcg aag ggt cgt aag cgc act cgc gaa  2210
              Val Pro Pro Lys Ala Lys Gly Arg Lys Arg Thr Arg Glu
                          565                 570

act gag aag ccg ctt tcc gga ctc gac gtc gat gcc ctg ctt cat cat    2258
Thr Glu Lys Pro Leu Ser Gly Leu Asp Val Asp Ala Leu Leu His His
575                 580                 585                 590

gaa aag cgc gcc aag ata tct ccc aac aat gcc att ccc gag ttc aag    2306
Glu Lys Arg Ala Lys Ile Ser Pro Asn Asn Ala Ile Pro Glu Phe Lys
                595                 600                 605

cag act ctc gca cag gcc gag aat atc gag gcc atc aaa gac gct aca    2354
Gln Thr Leu Ala Gln Ala Glu Asn Ile Glu Ala Ile Lys Asp Ala Thr
            610                 615                 620

aag cag atg atg gtt atc gtt gaa gat caa atc aaa cac agt ctc ggt    2402
Lys Gln Met Met Val Ile Val Glu Asp Gln Ile Lys His Ser Leu Gly
        625                 630                 635

gat gct aac tac gac cgg gtc att gaa gcg ctg ggc acg atg cgt gac    2450
Asp Ala Asn Tyr Asp Arg Val Ile Glu Ala Leu Gly Thr Met Arg Asp
    640                 645                 650

gag ttg gta tca tac gaa gag cct acc tcc tac aat aac ttc cta ggc    2498
Glu Leu Val Ser Tyr Glu Glu Pro Thr Ser Tyr Asn Asn Phe Leu Gly
655                 660                 665                 670

cag ctc aag gat aag ttg tta cag gag aag ctt gga gga gat cga caa    2546
Gln Leu Lys Asp Lys Leu Leu Gln Glu Lys Leu Gly Gly Asp Arg Gln
                675                 680                 685

gag ctg tgg tgg ctt att cga cga aac aag ctg gga ctt gtc act cag    2594
Glu Leu Trp Trp Leu Ile Arg Arg Asn Lys Leu Gly Leu Val Thr Gln
            690                 695                 700

cgc gag tcg gat caa tct agg gtt acc gat acg gaa gcc aaa gaa gta    2642
Arg Glu Ser Asp Gln Ser Arg Val Thr Asp Thr Glu Ala Lys Glu Val
        705                 710                 715

agt ctc att aag atg aag gag tga                                    2666
Ser Leu Ile Lys Met Lys Glu
    720                 725
```

```
<210> SEQ ID NO 6
<211> LENGTH: 725
<212> TYPE: PRT
<213> ORGANISM: Aspergillus sojae

<400> SEQUENCE: 6

Met Ala Asp Lys Glu Ala Thr Val Tyr Ile Val Asp Val Gly Arg Ser
```

-continued

```
1               5                   10                  15

Met Gly Glu Cys Arg Asn Gly Arg Ser Val Thr Asp Leu Glu Trp Ala
            20                  25                  30

Met Gln Tyr Val Trp Asp Arg Ile Thr Gly Thr Val Ala Thr Gly Arg
        35                  40                  45

Lys Thr Ala Thr Met Gly Val Ile Gly Leu Arg Thr Asp Glu Thr Ser
    50                  55                  60

Asn Glu Leu Glu Asp Asp Val His Phe Ser His Ile Ala Val Leu Ser
65                  70                  75                  80

Asn Ile Lys Gln Phe Leu Met Pro Asp Ile Arg Lys Leu Glu Asp Glu
                85                  90                  95

Leu Lys Pro Ser Lys Thr Asp Lys Gly Asp Ala Ile Ser Ala Ile Ile
            100                 105                 110

Leu Ala Ile Gln Met Ile Ile Thr His Cys Lys Lys Leu Lys Tyr Arg
        115                 120                 125

Arg Lys Ile Ala Leu Val Thr Asn Gly Gln Gly Arg Met Ser Asp Glu
    130                 135                 140

Asp Leu Gly Glu Ile Val Lys Lys Val Lys Glu Asp Asn Ile Glu Leu
145                 150                 155                 160

Val Val Met Gly Ile Asp Phe Asp Asp Pro Glu Tyr Gly Tyr Lys Glu
                165                 170                 175

Glu Asp Lys Asp Pro Arg Lys Ala Glu Asn Glu Thr Leu Leu Arg Thr
            180                 185                 190

Leu Val Glu Asp Cys Asp Gly Val Tyr Gly Thr Phe Glu Gln Ala Val
        195                 200                 205

Ala Glu Leu Asp Ile Pro Arg Val Lys Ser Val Arg Ser Val Ala Ser
    210                 215                 220

Phe Lys Gly Tyr Leu Gln Leu Gly Asn Pro Glu Asp Tyr Asp Ser Ala
225                 230                 235                 240

Leu Arg Ile Pro Val Glu Arg Tyr Tyr Arg Thr Tyr Pro Ala Lys Pro
                245                 250                 255

Pro Thr Ala Ser Ser Phe Val Leu Arg Ser Glu Pro Glu Ala Gly Gln
            260                 265                 270

Glu Glu Ala Glu Ser Ser Glu Ala Ala Ala Ala Thr Gln Lys Gly Ser
        275                 280                 285

Gln Ser Gly Asp Ile Gly Leu Thr Thr Val Arg Thr Met Arg Thr Tyr
    290                 295                 300

Gln Val Glu Asp Lys Ser Ala Pro Gly Gly Lys Ile Asp Ile Glu Arg
305                 310                 315                 320

Asp Asp Leu Ala Lys Gly Tyr Glu Tyr Gly Arg Thr Ala Val His Ile
                325                 330                 335

Ser Glu Thr Asp Glu Asn Ile Thr Ile Leu Asp Thr Phe Ala Gly Leu
            340                 345                 350

Glu Leu Met Gly Phe Ile Gln Thr Asp Arg Tyr Gln Arg Tyr Met His
        355                 360                 365

Met Ser Asn Thr Asn Ile Ile Ile Ala Gln Arg Ala Asn Asp Lys Ala
    370                 375                 380

Ala Leu Ala Leu Ser Ser Phe Ile His Ala Leu Phe Glu Leu Glu Cys
385                 390                 395                 400

Tyr Ala Val Ala Arg Leu Val Val Lys Glu Asn Lys Pro Pro Val Ile
                405                 410                 415

Val Leu Leu Ala Pro Ser Ile Glu Pro Asp Tyr Glu Cys Leu Leu Glu
            420                 425                 430
```

```
Val Gln Leu Pro Phe Ala Glu Asp Val Arg Thr Tyr Arg Phe Pro Pro
        435                 440                 445

Leu Asp Lys Val Ile Thr Val Ser Gly Lys Val Val Thr Gln His Arg
    450                 455                 460

Asn Leu Pro Asn Asp Asp Leu Leu Asp Val Met Gly Lys Tyr Val Asn
465                 470                 475                 480

Ser Met Glu Leu Val Asp Ala Asp Glu Asp Gly Asp Pro Val Glu Thr
                485                 490                 495

Phe Pro Ile Asp Asp Ser Tyr Ser Pro Val Leu His Arg Ile Asp Ala
            500                 505                 510

Ala Ile Arg Ala Arg Ala Ile His Pro Asp Gln Pro Ile Pro Pro Pro
        515                 520                 525

Ser Glu Arg Leu Thr Lys Phe Ser His Pro Arg Glu Asp Leu Ile Glu
    530                 535                 540

Arg Ser Gln Lys Tyr Leu Glu Lys Leu Ile Glu Ile Ala Asp Val Lys
545                 550                 555                 560

Lys Val Pro Pro Lys Ala Lys Gly Arg Lys Arg Thr Arg Glu Thr Glu
                565                 570                 575

Lys Pro Leu Ser Gly Leu Asp Val Asp Ala Leu Leu His His Glu Lys
            580                 585                 590

Arg Ala Lys Ile Ser Pro Asn Asn Ala Ile Pro Glu Phe Lys Gln Thr
        595                 600                 605

Leu Ala Gln Ala Glu Asn Ile Glu Ala Ile Lys Asp Ala Thr Lys Gln
    610                 615                 620

Met Met Val Ile Val Glu Asp Gln Ile Lys His Ser Leu Gly Asp Ala
625                 630                 635                 640

Asn Tyr Asp Arg Val Ile Glu Ala Leu Gly Thr Met Arg Asp Glu Leu
                645                 650                 655

Val Ser Tyr Glu Glu Pro Thr Ser Tyr Asn Asn Phe Leu Gly Gln Leu
            660                 665                 670

Lys Asp Lys Leu Leu Gln Glu Lys Leu Gly Gly Asp Arg Gln Glu Leu
        675                 680                 685

Trp Trp Leu Ile Arg Arg Asn Lys Leu Gly Leu Val Thr Gln Arg Glu
    690                 695                 700

Ser Asp Gln Ser Arg Val Thr Asp Thr Glu Ala Lys Glu Val Ser Leu
705                 710                 715                 720

Ile Lys Met Lys Glu
                725


<210> SEQ ID NO 7
<211> LENGTH: 2249
<212> TYPE: DNA
<213> ORGANISM: Aspergillus oryzae
<220> FEATURE:
<221> NAME/KEY: misc_feature
<223> OTHER INFORMATION: Aspergillus oryzae Ku70
<220> FEATURE:
<221> NAME/KEY: CDS
<222> LOCATION: (1)..(69)
<220> FEATURE:
<221> NAME/KEY: CDS
<222> LOCATION: (130)..(741)
<220> FEATURE:
<221> NAME/KEY: CDS
<222> LOCATION: (791)..(1637)
<223> OTHER INFORMATION: split codon
<220> FEATURE:
<221> NAME/KEY: CDS
<222> LOCATION: (1696)..(1799)
<223> OTHER INFORMATION: split codon
<220> FEATURE:
```

```
<221> NAME/KEY: CDS
<222> LOCATION: (1851)..(2078)
<220> FEATURE:
<221> NAME/KEY: CDS
<222> LOCATION: (2142)..(2246)

<400> SEQUENCE: 7

atg gct gac gag gat caa tat cgt gga gac gac cag atc gat gag gaa       48
Met Ala Asp Glu Asp Gln Tyr Arg Gly Asp Asp Gln Ile Asp Glu Glu
1               5                   10                  15

gag gag gag acc gac gag agt gtacacactt tcaaacacac ctgaaagctt          99
Glu Glu Glu Thr Asp Glu Ser
            20

cggaggctaa catgttatca accaaaatag gga tac aaa aca gtg aaa gat gcc     153
                                 Gly Tyr Lys Thr Val Lys Asp Ala
                                     25                  30

gtt ctt ttt gct atc gaa gtc agc gat tcg atg ctc acg cct cgt cca      201
Val Leu Phe Ala Ile Glu Val Ser Asp Ser Met Leu Thr Pro Arg Pro
            35                  40                  45

tct tcc gat tca aag aaa cct gcg gag gag tcc ccc aca acg gcc gca      249
Ser Ser Asp Ser Lys Lys Pro Ala Glu Glu Ser Pro Thr Thr Ala Ala
        50                  55                  60

cta aaa tgc gca tat tat ctc atg caa caa cgc att atc tct aat ccc      297
Leu Lys Cys Ala Tyr Tyr Leu Met Gln Gln Arg Ile Ile Ser Asn Pro
    65                  70                  75

cgt gac atg atc ggt gtg cta tta tat ggg acg cag gcg tcc aaa ttt      345
Arg Asp Met Ile Gly Val Leu Leu Tyr Gly Thr Gln Ala Ser Lys Phe
80                  85                  90                  95

tat gac gag gat gaa aat agt cga gga gat ctt tca tac cca cac tgc      393
Tyr Asp Glu Asp Glu Asn Ser Arg Gly Asp Leu Ser Tyr Pro His Cys
                100                 105                 110

tac ctt ttc aca gac ctt gat gtc ccc tct gcg caa gaa gtc aag aat      441
Tyr Leu Phe Thr Asp Leu Asp Val Pro Ser Ala Gln Glu Val Lys Asn
            115                 120                 125

ctt cgg gca cta gca caa gac ggc gat gaa tca aag gat gta ctt aag      489
Leu Arg Ala Leu Ala Gln Asp Gly Asp Glu Ser Lys Asp Val Leu Lys
        130                 135                 140

gcg tca ggc gag cgg gtc tca atg gcg aac gta ctc ttt tgc gcc aat      537
Ala Ser Gly Glu Arg Val Ser Met Ala Asn Val Leu Phe Cys Ala Asn
    145                 150                 155

caa ata ttc acg tcg aaa gcc cct aac ttc ttg tct cgg cga ttg ttt      585
Gln Ile Phe Thr Ser Lys Ala Pro Asn Phe Leu Ser Arg Arg Leu Phe
160                 165                 170                 175

ata gtc acc gat aat gat gac cct cat ggc gat aat aaa agc ttg aga      633
Ile Val Thr Asp Asn Asp Asp Pro His Gly Asp Asn Lys Ser Leu Arg
                180                 185                 190

tcc gct tca act gta cgc gcg aag gac tta tat gac ctc ggt gtc act      681
Ser Ala Ser Thr Val Arg Ala Lys Asp Leu Tyr Asp Leu Gly Val Thr
            195                 200                 205

att gag ctg ttt ccg att tct cgg cca ggc cat gag ttc gat acc gcc      729
Ile Glu Leu Phe Pro Ile Ser Arg Pro Gly His Glu Phe Asp Thr Ala
        210                 215                 220

aga ttc tat gac gtaagattat attgactcaa tgtgaagtat cgctgctaac          781
Arg Phe Tyr Asp
    225

agcaattag gat atc atc tac aag gcc tct cct tcg gat cca gat gcc ccg    832
          Asp Ile Ile Tyr Lys Ala Ser Pro Ser Asp Pro Asp Ala Pro
                  230                 235                 240

gca tac ctg caa acc gat tcc aag gct tct cca gcc acc ggg gat ggg      880
Ala Tyr Leu Gln Thr Asp Ser Lys Ala Ser Pro Ala Thr Gly Asp Gly
            245                 250                 255
```

-continued

```
ata tca ctg ctc aat acc ctc ctg tcc aat atc aat tca aga tct gtc      928
Ile Ser Leu Leu Asn Thr Leu Leu Ser Asn Ile Asn Ser Arg Ser Val
        260                 265                 270

cca cgg cgt gca cag ttc tcc aat ata cca ttg gag ctt gga cca aac      976
Pro Arg Arg Ala Gln Phe Ser Asn Ile Pro Leu Glu Leu Gly Pro Asn
    275                 280                 285

tta aaa ata tct gtc tca gga tat ctt ttg ttc aag cgt caa gca ccc     1024
Leu Lys Ile Ser Val Ser Gly Tyr Leu Leu Phe Lys Arg Gln Ala Pro
290                 295                 300                 305

gcc aga aac tcc ttc atc tgg ctc ggc ggt gaa cag ccc cag att gtc     1072
Ala Arg Asn Ser Phe Ile Trp Leu Gly Gly Glu Gln Pro Gln Ile Val
                310                 315                 320

aaa gga gtg acc act caa atc gct gac gac acg gct cgc acg att gaa     1120
Lys Gly Val Thr Thr Gln Ile Ala Asp Asp Thr Ala Arg Thr Ile Glu
            325                 330                 335

aag tgg gaa att aag aaa gct tat aag ttt ggc ggt gat cag gtt gct     1168
Lys Trp Glu Ile Lys Lys Ala Tyr Lys Phe Gly Gly Asp Gln Val Ala
        340                 345                 350

ttc acg ccc gaa gag atg aag tca ctg agg aac ttc ggt gat cct gtc     1216
Phe Thr Pro Glu Glu Met Lys Ser Leu Arg Asn Phe Gly Asp Pro Val
    355                 360                 365

atc cgt ata ata ggg ttc aag ccc ctc tct gca ctt ccg ttc tgg gcc     1264
Ile Arg Ile Ile Gly Phe Lys Pro Leu Ser Ala Leu Pro Phe Trp Ala
370                 375                 380                 385

aat atc aaa cac ccc tcc ttt ata tac cca tcg gaa gaa gat ttt gtg     1312
Asn Ile Lys His Pro Ser Phe Ile Tyr Pro Ser Glu Glu Asp Phe Val
                390                 395                 400

ggc tcc acg cgg gtt ttt tct gct ttg cat cag aca ctc ctc cgg gat     1360
Gly Ser Thr Arg Val Phe Ser Ala Leu His Gln Thr Leu Leu Arg Asp
            405                 410                 415

aaa aag gcc gca ctt gtc tgg ttc att gct cgt aaa aat gca agt cct     1408
Lys Lys Ala Ala Leu Val Trp Phe Ile Ala Arg Lys Asn Ala Ser Pro
        420                 425                 430

gtt ctg ggg gct atg gtc gcc gga gaa gag aaa cta gac gag agt ggc     1456
Val Leu Gly Ala Met Val Ala Gly Glu Glu Lys Leu Asp Glu Ser Gly
    435                 440                 445

gtc cag aag ttt cct cca gga atg tgg ata ata cct ctc ccg ttc gct     1504
Val Gln Lys Phe Pro Pro Gly Met Trp Ile Ile Pro Leu Pro Phe Ala
450                 455                 460                 465

gat gac gtc cgt caa aac cct gaa acc aca ctc cat gtt gca cct gag     1552
Asp Asp Val Arg Gln Asn Pro Glu Thr Thr Leu His Val Ala Pro Glu
                470                 475                 480

cca ttg atc gat caa atg cgg tat att gtc cag caa ttg caa ctt cca     1600
Pro Leu Ile Asp Gln Met Arg Tyr Ile Val Gln Gln Leu Gln Leu Pro
            485                 490                 495

aag gcg tct tac gac ccc ttt aag tac cct aat cca t gtaagcttct        1647
Lys Ala Ser Tyr Asp Pro Phe Lys Tyr Pro Asn Pro
        500                 505

gccaacttcc tgcacagaaa ctctggcatt aacctattgc tctgttag cc  ctc caa    1703
                                                     Ser Leu Gln

tgg cat tat cgc att cta caa gcc ttg gcg ttg gat gag gac ctc ccg     1751
Trp His Tyr Arg Ile Leu Gln Ala Leu Ala Leu Asp Glu Asp Leu Pro
        515                 520                 525

gag aag cca gaa gac aaa acg ttg ccc aga tat cgg cag atc gat aaa     1799
Glu Lys Pro Glu Asp Lys Thr Leu Pro Arg Tyr Arg Gln Ile Asp Lys
    530                 535                 540

gtatatcaca cattcctatt ctttccacgg atcttgctga ccttcgctta g cgc act    1856
                                                         Arg Thr
                                                         545

ggc gac tat gta ttg tct tgg gcc gac gag ttg gaa aag caa tac gcg     1904
```

```
Gly Asp Tyr Val Leu Ser Trp Ala Asp Glu Leu Glu Lys Gln Tyr Ala
            550                 555                 560

aaa ata tcg gca cat ggc ccg aag agc aca ctc gtc aaa cga agc gcc      1952
Lys Ile Ser Ala His Gly Pro Lys Ser Thr Leu Val Lys Arg Ser Ala
        565                 570                 575

aaa gac cga aca tct gaa gtc gag gat gca gcc cag aag cca tac aag      2000
Lys Asp Arg Thr Ser Glu Val Glu Asp Ala Ala Gln Lys Pro Tyr Lys
    580                 585                 590

aaa gtg aag gtg gag aca gac gag caa ggc gtt gaa gat gta gtg cga      2048
Lys Val Lys Val Glu Thr Asp Glu Gln Gly Val Glu Asp Val Val Arg
595                 600                 605                 610

gcc cat tac cag aag gga tcg cta tcg aag gtgactatta cctgcccccct       2098
Ala His Tyr Gln Lys Gly Ser Leu Ser Lys
                615                 620

aggctttaat ttggactaac taacgcgcgt gacttgtgtg tag ctt acg gta cct      2153
                                                Leu Thr Val Pro

gtc ctc aaa gac ttt ctg aat gcc cat gga cgc tcc gct gct ggg aag      2201
Val Leu Lys Asp Phe Leu Asn Ala His Gly Arg Ser Ala Ala Gly Lys
625                 630                 635                 640

aaa gct gat ctc gtt gag cgt gtg gag gag tat ttg gag cag aaa tga      2249
Lys Ala Asp Leu Val Glu Arg Val Glu Glu Tyr Leu Glu Gln Lys
                645                 650                 655


<210> SEQ ID NO 8
<211> LENGTH: 655
<212> TYPE: PRT
<213> ORGANISM: Aspergillus oryzae

<400> SEQUENCE: 8

Met Ala Asp Glu Asp Gln Tyr Arg Gly Asp Asp Gln Ile Asp Glu Glu
1               5                   10                  15

Glu Glu Glu Thr Asp Glu Ser Gly Tyr Lys Thr Val Lys Asp Ala Val
            20                  25                  30

Leu Phe Ala Ile Glu Val Ser Asp Ser Met Leu Thr Pro Arg Pro Ser
        35                  40                  45

Ser Asp Ser Lys Lys Pro Ala Glu Glu Ser Pro Thr Thr Ala Ala Leu
    50                  55                  60

Lys Cys Ala Tyr Tyr Leu Met Gln Gln Arg Ile Ile Ser Asn Pro Arg
65                  70                  75                  80

Asp Met Ile Gly Val Leu Leu Tyr Gly Thr Gln Ala Ser Lys Phe Tyr
                85                  90                  95

Asp Glu Asp Glu Asn Ser Arg Gly Asp Leu Ser Tyr Pro His Cys Tyr
            100                 105                 110

Leu Phe Thr Asp Leu Asp Val Pro Ser Ala Gln Glu Val Lys Asn Leu
        115                 120                 125

Arg Ala Leu Ala Gln Asp Gly Asp Glu Ser Lys Asp Val Leu Lys Ala
    130                 135                 140

Ser Gly Glu Arg Val Ser Met Ala Asn Val Leu Phe Cys Ala Asn Gln
145                 150                 155                 160

Ile Phe Thr Ser Lys Ala Pro Asn Phe Leu Ser Arg Arg Leu Phe Ile
                165                 170                 175

Val Thr Asp Asn Asp Asp Pro His Gly Asp Asn Lys Ser Leu Arg Ser
            180                 185                 190

Ala Ser Thr Val Arg Ala Lys Asp Leu Tyr Asp Leu Gly Val Thr Ile
        195                 200                 205

Glu Leu Phe Pro Ile Ser Arg Pro Gly His Glu Phe Asp Thr Ala Arg
    210                 215                 220
```

```
Phe Tyr Asp Asp Ile Ile Tyr Lys Ala Ser Pro Ser Asp Pro Asp Ala
225                 230                 235                 240

Pro Ala Tyr Leu Gln Thr Asp Ser Lys Ala Ser Pro Ala Thr Gly Asp
                245                 250                 255

Gly Ile Ser Leu Leu Asn Thr Leu Leu Ser Asn Ile Asn Ser Arg Ser
            260                 265                 270

Val Pro Arg Arg Ala Gln Phe Ser Asn Ile Pro Leu Glu Leu Gly Pro
        275                 280                 285

Asn Leu Lys Ile Ser Val Ser Gly Tyr Leu Leu Phe Lys Arg Gln Ala
    290                 295                 300

Pro Ala Arg Asn Ser Phe Ile Trp Leu Gly Gly Glu Gln Pro Gln Ile
305                 310                 315                 320

Val Lys Gly Val Thr Thr Gln Ile Ala Asp Asp Thr Ala Arg Thr Ile
                325                 330                 335

Glu Lys Trp Glu Ile Lys Lys Ala Tyr Lys Phe Gly Gly Asp Gln Val
            340                 345                 350

Ala Phe Thr Pro Glu Glu Met Lys Ser Leu Arg Asn Phe Gly Asp Pro
        355                 360                 365

Val Ile Arg Ile Ile Gly Phe Lys Pro Leu Ser Ala Leu Pro Phe Trp
    370                 375                 380

Ala Asn Ile Lys His Pro Ser Phe Ile Tyr Pro Ser Glu Glu Asp Phe
385                 390                 395                 400

Val Gly Ser Thr Arg Val Phe Ser Ala Leu His Gln Thr Leu Leu Arg
                405                 410                 415

Asp Lys Lys Ala Ala Leu Val Trp Phe Ile Ala Arg Lys Asn Ala Ser
            420                 425                 430

Pro Val Leu Gly Ala Met Val Ala Gly Glu Glu Lys Leu Asp Glu Ser
        435                 440                 445

Gly Val Gln Lys Phe Pro Pro Gly Met Trp Ile Ile Pro Leu Pro Phe
    450                 455                 460

Ala Asp Asp Val Arg Gln Asn Pro Glu Thr Thr Leu His Val Ala Pro
465                 470                 475                 480

Glu Pro Leu Ile Asp Gln Met Arg Tyr Ile Val Gln Gln Leu Gln Leu
                485                 490                 495

Pro Lys Ala Ser Tyr Asp Pro Phe Lys Tyr Pro Asn Pro Ser Leu Gln
            500                 505                 510

Trp His Tyr Arg Ile Leu Gln Ala Leu Ala Leu Asp Glu Asp Leu Pro
        515                 520                 525

Glu Lys Pro Glu Asp Lys Thr Leu Pro Arg Tyr Arg Gln Ile Asp Lys
    530                 535                 540

Arg Thr Gly Asp Tyr Val Leu Ser Trp Ala Asp Glu Leu Glu Lys Gln
545                 550                 555                 560

Tyr Ala Lys Ile Ser Ala His Gly Pro Lys Ser Thr Leu Val Lys Arg
                565                 570                 575

Ser Ala Lys Asp Arg Thr Ser Glu Val Glu Asp Ala Ala Gln Lys Pro
            580                 585                 590

Tyr Lys Lys Val Lys Val Glu Thr Asp Glu Gln Gly Val Glu Asp Val
        595                 600                 605

Val Arg Ala His Tyr Gln Lys Gly Ser Leu Ser Lys Leu Thr Val Pro
    610                 615                 620

Val Leu Lys Asp Phe Leu Asn Ala His Gly Arg Ser Ala Ala Gly Lys
625                 630                 635                 640

Lys Ala Asp Leu Val Glu Arg Val Glu Glu Tyr Leu Glu Gln Lys
                645                 650                 655
```

```
<210> SEQ ID NO 9
<211> LENGTH: 2703
<212> TYPE: DNA
<213> ORGANISM: Aspergillus oryzae
<220> FEATURE:
<221> NAME/KEY: misc_feature
<223> OTHER INFORMATION: Aspergillus oryzae Ku80 Long
<220> FEATURE:
<221> NAME/KEY: CDS
<222> LOCATION: (1)..(129)
<220> FEATURE:
<221> NAME/KEY: CDS
<222> LOCATION: (192)..(246)
<223> OTHER INFORMATION: split codon
<220> FEATURE:
<221> NAME/KEY: CDS
<222> LOCATION: (300)..(366)
<223> OTHER INFORMATION: split codon
<220> FEATURE:
<221> NAME/KEY: CDS
<222> LOCATION: (425)..(492)
<223> OTHER INFORMATION: split codon
<220> FEATURE:
<221> NAME/KEY: CDS
<222> LOCATION: (552)..(720)
<223> OTHER INFORMATION: split codon
<220> FEATURE:
<221> NAME/KEY: CDS
<222> LOCATION: (772)..(832)
<223> OTHER INFORMATION: split codon
<220> FEATURE:
<221> NAME/KEY: CDS
<222> LOCATION: (882)..(1418)
<220> FEATURE:
<221> NAME/KEY: CDS
<222> LOCATION: (1469)..(1854)
<223> OTHER INFORMATION: split codon
<220> FEATURE:
<221> NAME/KEY: CDS
<222> LOCATION: (1905)..(2116)
<223> OTHER INFORMATION: split codon
<220> FEATURE:
<221> NAME/KEY: CDS
<222> LOCATION: (2169)..(2635)
<223> OTHER INFORMATION: split codon
<220> FEATURE:
<221> NAME/KEY: CDS
<222> LOCATION: (2686)..(2700)

<400> SEQUENCE: 9

atg gcg gac aag gaa gca act gtg tat att gtg gac gtt ggg agg tcc       48
Met Ala Asp Lys Glu Ala Thr Val Tyr Ile Val Asp Val Gly Arg Ser
1               5                   10                  15

atg gga gaa tgt cgc aat ggc cga tca gtg act gat ctt gaa tgg gcc       96
Met Gly Glu Cys Arg Asn Gly Arg Ser Val Thr Asp Leu Glu Trp Ala
            20                  25                  30

atg cag tat gtc tgg gat cgc att aca gga aca gtgagtggca gtcgtcacaa    149
Met Gln Tyr Val Trp Asp Arg Ile Thr Gly Thr
        35                  40

ttggaccgta ttcgttaaat accttgctca atttcaaacc ag gtg gcc act ggc       203
                                               Val Ala Thr Gly
                                                   45

cgc aaa act gcc atg atg ggt gtg att gga ctc agg aca gat g            246
Arg Lys Thr Ala Met Met Gly Val Ile Gly Leu Arg Thr Asp
        50                  55                  60

gtatgtatac ttctgaatac tgtatgcggt tcatacgctg atccaaaaat tag aa        301
                                                        Glu

acg tcc aac gaa ctt gaa gat gac gta cat ttc tct cac att gca gtt      349
Thr Ser Asn Glu Leu Glu Asp Asp Val His Phe Ser His Ile Ala Val
        65                  70                  75
```

```
ctg tcg aac ctc aaa ca  gtatgctttc cactctatga taatttggtt           396
Leu Ser Asn Leu Lys Gln
    80

tgtgcgccaa actgacgagg acgtcaag g ttt ctt atg ccg gac att cgg aaa     449
                                 Phe Leu Met Pro Asp Ile Arg Lys
                                 85                  90

ctg gaa gat gaa ctg aaa ccg agc aaa acg gac aaa gga gac g            492
Leu Glu Asp Glu Leu Lys Pro Ser Lys Thr Asp Lys Gly Asp
        95                  100                 105

gtaagctttt tgagagccac taggacctac tgtccaattt actaaacttt gttctctag     551

ct  att tcc gct att atc ttg gct att cag atg att atc acg cat tgc     598
Ala Ile Ser Ala Ile Ile Leu Ala Ile Gln Met Ile Ile Thr His Cys
            110                 115                 120

aag aag ttg aag tac agg cgc aag atc gtc ctc gtc act aac gga cag     646
Lys Lys Leu Lys Tyr Arg Arg Lys Ile Val Leu Val Thr Asn Gly Gln
        125                 130                 135

ggg cgc atg agc gat gaa gac ctg ggc gag att gtg aag aag gtc aag     694
Gly Arg Met Ser Asp Glu Asp Leu Gly Glu Ile Val Lys Lys Val Lys
    140                 145                 150

gaa gat aac atc gag ctt gtt gtt at  gtcagtgatt tgctaccaga           740
Glu Asp Asn Ile Glu Leu Val Val Met
155                 160

tagcaacgaa acaaaagcta acttcaagca g g gga att gat ttc gat gac cct     793
                                     Gly Ile Asp Phe Asp Asp Pro
                                         165                 170

gag tac ggt tac aaa gaa gaa gac aaa gac cct cac aag gtagcgatat       842
Glu Tyr Gly Tyr Lys Glu Glu Asp Lys Asp Pro His Lys
                175                 180

ctctcgcgca gctttgttct tttctaacaa ctaaaacag gcc gaa aat gaa act       896
                                           Ala Glu Asn Glu Thr
                                               185

ctc ttg cgt acc ctt gtg gaa gat tgt gat gga gtc tat gga aca ttc     944
Leu Leu Arg Thr Leu Val Glu Asp Cys Asp Gly Val Tyr Gly Thr Phe
    190                 195                 200

gag cag gct gtg gct gaa cta gac atc ccc cgt gtc aag tct gtc agg     992
Glu Gln Ala Val Ala Glu Leu Asp Ile Pro Arg Val Lys Ser Val Arg
205                 210                 215                 220

tca gtg gca agc ttc aaa gga tat ctc caa cta ggc aac cca gag gag    1040
Ser Val Ala Ser Phe Lys Gly Tyr Leu Gln Leu Gly Asn Pro Glu Glu
                225                 230                 235

tat gac tct gct ctc cgc att cct gtt gaa agg tac tat cgg act tac    1088
Tyr Asp Ser Ala Leu Arg Ile Pro Val Glu Arg Tyr Tyr Arg Thr Tyr
            240                 245                 250

ccg gcc aaa ccc ccg acc gca agt tct ttc gtc ctg cgc tca gag cct    1136
Pro Ala Lys Pro Pro Thr Ala Ser Ser Phe Val Leu Arg Ser Glu Pro
        255                 260                 265

gaa gct gga caa gaa gag gca gag tca tct gag gct gct gct gct acg    1184
Glu Ala Gly Gln Glu Glu Ala Glu Ser Ser Glu Ala Ala Ala Ala Thr
    270                 275                 280

caa aaa ggg agc caa tct gga gat gcc gga ttg acc act gtg aga acc    1232
Gln Lys Gly Ser Gln Ser Gly Asp Ala Gly Leu Thr Thr Val Arg Thr
285                 290                 295                 300

atg aga aca tat caa gtt gag gac aaa agt gca ccg ggt ggg aaa atc    1280
Met Arg Thr Tyr Gln Val Glu Asp Lys Ser Ala Pro Gly Gly Lys Ile
                305                 310                 315

gac atc gaa cga gat gag ctc gcc aaa gga tat gag tat gga cgg aca    1328
Asp Ile Glu Arg Asp Glu Leu Ala Lys Gly Tyr Glu Tyr Gly Arg Thr
            320                 325                 330

gca gtt cac att agt gaa act gac gag aac atc acg att ctc gat aca    1376
Ala Val His Ile Ser Glu Thr Asp Glu Asn Ile Thr Ile Leu Asp Thr
```

```
        335                 340                 345

ttc gca ggg ctg gag ttg atg ggc ttc atc cag act gac cag             1418
Phe Ala Gly Leu Glu Leu Met Gly Phe Ile Gln Thr Asp Gln
    350                 355                 360

gtatgtcttg ctgaagtcgc ctcggtgcat gctctgacac acgattatag tat caa      1474
                                                       Tyr Gln

cgt tat atg cac atg tcc aac aca aac atc ata att gca caa cgt gcc     1522
Arg Tyr Met His Met Ser Asn Thr Asn Ile Ile Ile Ala Gln Arg Ala
365                 370                 375                 380

aac gac aaa gca gct ctt gcc ctt tca tcc ttt ata cac gcc ctt ttt     1570
Asn Asp Lys Ala Ala Leu Ala Leu Ser Ser Phe Ile His Ala Leu Phe
                385                 390                 395

gag cta gaa tgc tat gct gtt gct cgc cta gtt gtg aaa gag aac aag     1618
Glu Leu Glu Cys Tyr Ala Val Ala Arg Leu Val Val Lys Glu Asn Lys
            400                 405                 410

cca cca gtt ata gtc ttg ctc gcg ccc tcg atc gag cct gag tat gaa     1666
Pro Pro Val Ile Val Leu Leu Ala Pro Ser Ile Glu Pro Glu Tyr Glu
        415                 420                 425

tgc ctt ctc gaa gtc cag tta cca ttt gcg gaa gat gtc cga acc tat     1714
Cys Leu Leu Glu Val Gln Leu Pro Phe Ala Glu Asp Val Arg Thr Tyr
    430                 435                 440

cgg ttc cct cct ctg gat aaa gtg att act gtt tcc gga aag gtt gtg     1762
Arg Phe Pro Pro Leu Asp Lys Val Ile Thr Val Ser Gly Lys Val Val
445                 450                 455                 460

aca caa cac cgg aat ctt ccc agt gat gat tta ctc gat gtg atg ggc     1810
Thr Gln His Arg Asn Leu Pro Ser Asp Asp Leu Leu Asp Val Met Gly
                465                 470                 475

aag tac gtg aat agt atg gag ctt gtc gac gca gat gag gat gg          1854
Lys Tyr Val Asn Ser Met Glu Leu Val Asp Ala Asp Glu Asp Gly
            480                 485                 490

gtaggtttat gcctaaaaga ttccgaatat cttctcattg acataaccag g gat cca    1911
                                                         Asp Pro

gtg gag act ttc cct atc gac gac tcg tat tcc cca gtt ttg cac cgg     1959
Val Glu Thr Phe Pro Ile Asp Asp Ser Tyr Ser Pro Val Leu His Arg
    495                 500                 505

att gac gcc gcc atc cgt gct cgg gct ata cat cct gac cag ccc ata     2007
Ile Asp Ala Ala Ile Arg Ala Arg Ala Ile His Pro Asp Gln Pro Ile
510                 515                 520                 525

cct cct cca tca gag aga ctg aca aaa ttc tca cac cca cga gag gat     2055
Pro Pro Pro Ser Glu Arg Leu Thr Lys Phe Ser His Pro Arg Glu Asp
                530                 535                 540

ctc atc gag aaa tca cag aaa cac cta gag aag ttg atc gag ata gcc     2103
Leu Ile Glu Lys Ser Gln Lys His Leu Glu Lys Leu Ile Glu Ile Ala
            545                 550                 555

gat gtt aag aag g gttggacatc accccacaat caagtctgtc agactgctaa       2156
Asp Val Lys Lys
        560

ttcagttacc ag tt  cct ccc aaa gcg aag ggt cgc aag cgc act cgt gaa   2206
              Val Pro Pro Lys Ala Lys Gly Arg Lys Arg Thr Arg Glu
                          565                 570

acc gaa aag cca ctt tcc gga ctc gac gtc gat gcc ctg ctt cat cat     2254
Thr Glu Lys Pro Leu Ser Gly Leu Asp Val Asp Ala Leu Leu His His
575                 580                 585                 590

gaa aag cgc gtc aag ata tct ccc aac aat gcc att cct gag ttc aag     2302
Glu Lys Arg Val Lys Ile Ser Pro Asn Asn Ala Ile Pro Glu Phe Lys
                595                 600                 605

cag act ctc gca cag gcc gag aat atc gag gcc atc aaa gac gct aca     2350
Gln Thr Leu Ala Gln Ala Glu Asn Ile Glu Ala Ile Lys Asp Ala Thr
            610                 615                 620
```

-continued

```
aag cag atg atg gtc atc gtt gaa gat caa atc aaa cac agt ctc ggt      2398
Lys Gln Met Met Val Ile Val Glu Asp Gln Ile Lys His Ser Leu Gly
        625                 630                 635

aat gct aac tac gac cgg gtc att gaa gcg ctg ggc acg atg cgt gac      2446
Asn Ala Asn Tyr Asp Arg Val Ile Glu Ala Leu Gly Thr Met Arg Asp
    640                 645                 650

gag ttg gta tct tac gaa gag cct gcc tcc tac aat gac ttc ctg ggc      2494
Glu Leu Val Ser Tyr Glu Glu Pro Ala Ser Tyr Asn Asp Phe Leu Gly
655                 660                 665                 670

cag ctc aag gat aag tta ctg cag gag aag ctt gga gga gac cga caa      2542
Gln Leu Lys Asp Lys Leu Leu Gln Glu Lys Leu Gly Gly Asp Arg Gln
                675                 680                 685

gag ctg tgg tgg ctt gtt cga cga aac aag ctg gga ctt gtc act cag      2590
Glu Leu Trp Trp Leu Val Arg Arg Asn Lys Leu Gly Leu Val Thr Gln
            690                 695                 700

cgc gag tcg gat caa tct agg gtt acc gat acg gaa gcc aaa gaa          2635
Arg Glu Ser Asp Gln Ser Arg Val Thr Asp Thr Glu Ala Lys Glu
        705                 710                 715

gtaagtctca ctaagatgaa ggagtgacct agactaactg cagtttacag ttc atg      2691
                                                       Phe Met

tcc gcc aga tga                                                      2703
Ser Ala Arg
720


<210> SEQ ID NO 10
<211> LENGTH: 722
<212> TYPE: PRT
<213> ORGANISM: Aspergillus oryzae

<400> SEQUENCE: 10

Met Ala Asp Lys Glu Ala Thr Val Tyr Ile Val Asp Val Gly Arg Ser
1               5                   10                  15

Met Gly Glu Cys Arg Asn Gly Arg Ser Val Thr Asp Leu Glu Trp Ala
            20                  25                  30

Met Gln Tyr Val Trp Asp Arg Ile Thr Gly Thr Val Ala Thr Gly Arg
        35                  40                  45

Lys Thr Ala Met Met Gly Val Ile Gly Leu Arg Thr Asp Glu Thr Ser
    50                  55                  60

Asn Glu Leu Glu Asp Asp Val His Phe Ser His Ile Ala Val Leu Ser
65                  70                  75                  80

Asn Leu Lys Gln Phe Leu Met Pro Asp Ile Arg Lys Leu Glu Asp Glu
                85                  90                  95

Leu Lys Pro Ser Lys Thr Asp Lys Gly Asp Ala Ile Ser Ala Ile Ile
            100                 105                 110

Leu Ala Ile Gln Met Ile Ile Thr His Cys Lys Lys Leu Lys Tyr Arg
        115                 120                 125

Arg Lys Ile Val Leu Val Thr Asn Gly Gln Gly Arg Met Ser Asp Glu
    130                 135                 140

Asp Leu Gly Glu Ile Val Lys Lys Val Lys Glu Asp Asn Ile Glu Leu
145                 150                 155                 160

Val Val Met Gly Ile Asp Phe Asp Asp Pro Glu Tyr Gly Tyr Lys Glu
                165                 170                 175

Glu Asp Lys Asp Pro His Lys Ala Glu Asn Glu Thr Leu Leu Arg Thr
            180                 185                 190

Leu Val Glu Asp Cys Asp Gly Val Tyr Gly Thr Phe Glu Gln Ala Val
        195                 200                 205

Ala Glu Leu Asp Ile Pro Arg Val Lys Ser Val Arg Ser Val Ala Ser
    210                 215                 220
```

```
Phe Lys Gly Tyr Leu Gln Leu Gly Asn Pro Glu Glu Tyr Asp Ser Ala
225                 230                 235                 240

Leu Arg Ile Pro Val Glu Arg Tyr Tyr Arg Thr Tyr Pro Ala Lys Pro
                245                 250                 255

Pro Thr Ala Ser Ser Phe Val Leu Arg Ser Glu Pro Glu Ala Gly Gln
            260                 265                 270

Glu Glu Ala Glu Ser Ser Glu Ala Ala Ala Ala Thr Gln Lys Gly Ser
        275                 280                 285

Gln Ser Gly Asp Ala Gly Leu Thr Thr Val Arg Thr Met Arg Thr Tyr
    290                 295                 300

Gln Val Glu Asp Lys Ser Ala Pro Gly Gly Lys Ile Asp Ile Glu Arg
305                 310                 315                 320

Asp Glu Leu Ala Lys Gly Tyr Glu Tyr Gly Arg Thr Ala Val His Ile
                325                 330                 335

Ser Glu Thr Asp Glu Asn Ile Thr Ile Leu Asp Thr Phe Ala Gly Leu
            340                 345                 350

Glu Leu Met Gly Phe Ile Gln Thr Asp Gln Tyr Gln Arg Tyr Met His
        355                 360                 365

Met Ser Asn Thr Asn Ile Ile Ile Ala Gln Arg Ala Asn Asp Lys Ala
    370                 375                 380

Ala Leu Ala Leu Ser Ser Phe Ile His Ala Leu Phe Glu Leu Glu Cys
385                 390                 395                 400

Tyr Ala Val Ala Arg Leu Val Val Lys Glu Asn Lys Pro Pro Val Ile
                405                 410                 415

Val Leu Leu Ala Pro Ser Ile Glu Pro Glu Tyr Glu Cys Leu Leu Glu
            420                 425                 430

Val Gln Leu Pro Phe Ala Glu Asp Val Arg Thr Tyr Arg Phe Pro Pro
        435                 440                 445

Leu Asp Lys Val Ile Thr Val Ser Gly Lys Val Val Thr Gln His Arg
    450                 455                 460

Asn Leu Pro Ser Asp Asp Leu Leu Asp Val Met Gly Lys Tyr Val Asn
465                 470                 475                 480

Ser Met Glu Leu Val Asp Ala Asp Glu Asp Gly Asp Pro Val Glu Thr
                485                 490                 495

Phe Pro Ile Asp Asp Ser Tyr Ser Pro Val Leu His Arg Ile Asp Ala
            500                 505                 510

Ala Ile Arg Ala Arg Ala Ile His Pro Asp Gln Pro Ile Pro Pro Pro
        515                 520                 525

Ser Glu Arg Leu Thr Lys Phe Ser His Pro Arg Glu Asp Leu Ile Glu
    530                 535                 540

Lys Ser Gln Lys His Leu Glu Lys Leu Ile Glu Ile Ala Asp Val Lys
545                 550                 555                 560

Lys Val Pro Pro Lys Ala Lys Gly Arg Lys Arg Thr Arg Glu Thr Glu
                565                 570                 575

Lys Pro Leu Ser Gly Leu Asp Val Asp Ala Leu Leu His His Glu Lys
            580                 585                 590

Arg Val Lys Ile Ser Pro Asn Asn Ala Ile Pro Glu Phe Lys Gln Thr
        595                 600                 605

Leu Ala Gln Ala Glu Asn Ile Glu Ala Ile Lys Asp Ala Thr Lys Gln
    610                 615                 620

Met Met Val Ile Val Glu Asp Gln Ile Lys His Ser Leu Gly Asn Ala
625                 630                 635                 640

Asn Tyr Asp Arg Val Ile Glu Ala Leu Gly Thr Met Arg Asp Glu Leu
```

```
                645                 650                 655

Val Ser Tyr Glu Glu Pro Ala Ser Tyr Asn Asp Phe Leu Gly Gln Leu
            660                 665                 670

Lys Asp Lys Leu Leu Gln Glu Lys Leu Gly Gly Asp Arg Gln Glu Leu
        675                 680                 685

Trp Trp Leu Val Arg Arg Asn Lys Leu Gly Leu Val Thr Gln Arg Glu
    690                 695                 700

Ser Asp Gln Ser Arg Val Thr Asp Thr Glu Ala Lys Glu Phe Met Ser
705                 710                 715                 720

Ala Arg


<210> SEQ ID NO 11
<211> LENGTH: 2662
<212> TYPE: DNA
<213> ORGANISM: Aspergillus oryzae
<220> FEATURE:
<221> NAME/KEY: misc_feature
<223> OTHER INFORMATION: Aspergillus oryzae Ku80 Short
<220> FEATURE:
<221> NAME/KEY: CDS
<222> LOCATION: (1)..(129)
<220> FEATURE:
<221> NAME/KEY: CDS
<222> LOCATION: (192)..(246)
<223> OTHER INFORMATION: split codon
<220> FEATURE:
<221> NAME/KEY: CDS
<222> LOCATION: (300)..(366)
<223> OTHER INFORMATION: split codon
<220> FEATURE:
<221> NAME/KEY: CDS
<222> LOCATION: (425)..(492)
<223> OTHER INFORMATION: split codon
<220> FEATURE:
<221> NAME/KEY: CDS
<222> LOCATION: (552)..(720)
<223> OTHER INFORMATION: split codon
<220> FEATURE:
<221> NAME/KEY: CDS
<222> LOCATION: (772)..(832)
<223> OTHER INFORMATION: split codon
<220> FEATURE:
<221> NAME/KEY: CDS
<222> LOCATION: (882)..(1418)
<220> FEATURE:
<221> NAME/KEY: CDS
<222> LOCATION: (1469)..(1854)
<223> OTHER INFORMATION: split codon
<220> FEATURE:
<221> NAME/KEY: CDS
<222> LOCATION: (1905)..(2116)
<223> OTHER INFORMATION: split codon
<220> FEATURE:
<221> NAME/KEY: CDS
<222> LOCATION: (2169)..(2659)
<223> OTHER INFORMATION: split codon

<400> SEQUENCE: 11

atg gcg gac aag gaa gca act gtg tat att gtg gac gtt ggg agg tcc       48
Met Ala Asp Lys Glu Ala Thr Val Tyr Ile Val Asp Val Gly Arg Ser
1               5                   10                  15

atg gga gaa tgt cgc aat ggc cga tca gtg act gat ctt gaa tgg gcc       96
Met Gly Glu Cys Arg Asn Gly Arg Ser Val Thr Asp Leu Glu Trp Ala
            20                  25                  30

atg cag tat gtc tgg gat cgc att aca gga aca gtgagtggca gtcgtcacaa    149
Met Gln Tyr Val Trp Asp Arg Ile Thr Gly Thr
        35                  40

ttggaccgta ttcgttaaat accttgctca atttcaaacc ag gtg gcc act ggc       203
                                               Val Ala Thr Gly
                                                   45
```

```
cgc aaa act gcc atg atg ggt gtg att gga ctc agg aca gat g           246
Arg Lys Thr Ala Met Met Gly Val Ile Gly Leu Arg Thr Asp
        50                  55                  60

gtatgtatac ttctgaatac tgtatgcggt tcatacgctg atccaaaaat tag aa       301
                                                       Glu

acg tcc aac gaa ctt gaa gat gac gta cat ttc tct cac att gca gtt     349
Thr Ser Asn Glu Leu Glu Asp Asp Val His Phe Ser His Ile Ala Val
        65                  70                  75

ctg tcg aac ctc aaa ca  gtatgctttc cactctatga taatttggtt            396
Leu Ser Asn Leu Lys Gln
    80

tgtgcgccaa actgacgagg acgtcaag g ttt ctt atg ccg gac att cgg aaa    449
                                 Phe Leu Met Pro Asp Ile Arg Lys
                                 85                  90

ctg gaa gat gaa ctg aaa ccg agc aaa acg gac aaa gga gac g           492
Leu Glu Asp Glu Leu Lys Pro Ser Lys Thr Asp Lys Gly Asp
        95                  100                 105

gtaagctttt tgagagccac taggacctac tgtccaattt actaaacttt gttctctag    551

ct  att tcc gct att atc ttg gct att cag atg att atc acg cat tgc     598
Ala Ile Ser Ala Ile Ile Leu Ala Ile Gln Met Ile Ile Thr His Cys
            110                 115                 120

aag aag ttg aag tac agg cgc aag atc gtc ctc gtc act aac gga cag     646
Lys Lys Leu Lys Tyr Arg Arg Lys Ile Val Leu Val Thr Asn Gly Gln
        125                 130                 135

ggg cgc atg agc gat gaa gac ctg ggc gag att gtg aag aag gtc aag     694
Gly Arg Met Ser Asp Glu Asp Leu Gly Glu Ile Val Lys Lys Val Lys
    140                 145                 150

gaa gat aac atc gag ctt gtt gtt at  gtcagtgatt tgctaccaga           740
Glu Asp Asn Ile Glu Leu Val Val Met
155                 160

tagcaacgaa acaaaagcta acttcaagca g g gga att gat ttc gat gac cct    793
                                     Gly Ile Asp Phe Asp Asp Pro
                                         165                 170

gag tac ggt tac aaa gaa gaa gac aaa gac cct cac aag gtagcgatat      842
Glu Tyr Gly Tyr Lys Glu Glu Asp Lys Asp Pro His Lys
                175                 180

ctctcgcgca gctttgttct tttctaacaa ctaaaacag gcc gaa aat gaa act      896
                                           Ala Glu Asn Glu Thr
                                               185

ctc ttg cgt acc ctt gtg gaa gat tgt gat gga gtc tat gga aca ttc     944
Leu Leu Arg Thr Leu Val Glu Asp Cys Asp Gly Val Tyr Gly Thr Phe
    190                 195                 200

gag cag gct gtg gct gaa cta gac atc ccc cgt gtc aag tct gtc agg     992
Glu Gln Ala Val Ala Glu Leu Asp Ile Pro Arg Val Lys Ser Val Arg
205                 210                 215                 220

tca gtg gca agc ttc aaa gga tat ctc caa cta ggc aac cca gag gag    1040
Ser Val Ala Ser Phe Lys Gly Tyr Leu Gln Leu Gly Asn Pro Glu Glu
                225                 230                 235

tat gac tct gct ctc cgc att cct gtt gaa agg tac tat cgg act tac    1088
Tyr Asp Ser Ala Leu Arg Ile Pro Val Glu Arg Tyr Tyr Arg Thr Tyr
            240                 245                 250

ccg gcc aaa ccc ccg acc gca agt tct ttc gtc ctg cgc tca gag cct    1136
Pro Ala Lys Pro Pro Thr Ala Ser Ser Phe Val Leu Arg Ser Glu Pro
        255                 260                 265

gaa gct gga caa gaa gag gca gag tca tct gag gct gct gct gct acg    1184
Glu Ala Gly Gln Glu Glu Ala Glu Ser Ser Glu Ala Ala Ala Ala Thr
    270                 275                 280

caa aaa ggg agc caa tct gga gat gcc gga ttg acc act gtg aga acc    1232
Gln Lys Gly Ser Gln Ser Gly Asp Ala Gly Leu Thr Thr Val Arg Thr
```

-continued

```
285                 290                 295                 300

atg aga aca tat caa gtt gag gac aaa agt gca ccg ggt ggg aaa atc      1280
Met Arg Thr Tyr Gln Val Glu Asp Lys Ser Ala Pro Gly Gly Lys Ile
                305                 310                 315

gac atc gaa cga gat gag ctc gcc aaa gga tat gag tat gga cgg aca      1328
Asp Ile Glu Arg Asp Glu Leu Ala Lys Gly Tyr Glu Tyr Gly Arg Thr
            320                 325                 330

gca gtt cac att agt gaa act gac gag aac atc acg att ctc gat aca      1376
Ala Val His Ile Ser Glu Thr Asp Glu Asn Ile Thr Ile Leu Asp Thr
        335                 340                 345

ttc gca ggg ctg gag ttg atg ggc ttc atc cag act gac cag              1418
Phe Ala Gly Leu Glu Leu Met Gly Phe Ile Gln Thr Asp Gln
    350                 355                 360

gtatgtcttg ctgaagtcgc ctcggtgcat gctctgacac acgattatag tat caa      1474
                                                       Tyr Gln

cgt tat atg cac atg tcc aac aca aac atc ata att gca caa cgt gcc      1522
Arg Tyr Met His Met Ser Asn Thr Asn Ile Ile Ile Ala Gln Arg Ala
365                 370                 375                 380

aac gac aaa gca gct ctt gcc ctt tca tcc ttt ata cac gcc ctt ttt      1570
Asn Asp Lys Ala Ala Leu Ala Leu Ser Ser Phe Ile His Ala Leu Phe
                385                 390                 395

gag cta gaa tgc tat gct gtt gct cgc cta gtt gtg aaa gag aac aag      1618
Glu Leu Glu Cys Tyr Ala Val Ala Arg Leu Val Val Lys Glu Asn Lys
            400                 405                 410

cca cca gtt ata gtc ttg ctc gcg ccc tcg atc gag cct gag tat gaa      1666
Pro Pro Val Ile Val Leu Leu Ala Pro Ser Ile Glu Pro Glu Tyr Glu
        415                 420                 425

tgc ctt ctc gaa gtc cag tta cca ttt gcg gaa gat gtc cga acc tat      1714
Cys Leu Leu Glu Val Gln Leu Pro Phe Ala Glu Asp Val Arg Thr Tyr
    430                 435                 440

cgg ttc cct cct ctg gat aaa gtg att act gtt tcc gga aag gtt gtg      1762
Arg Phe Pro Pro Leu Asp Lys Val Ile Thr Val Ser Gly Lys Val Val
445                 450                 455                 460

aca caa cac cgg aat ctt ccc agt gat gat tta ctc gat gtg atg ggc      1810
Thr Gln His Arg Asn Leu Pro Ser Asp Asp Leu Leu Asp Val Met Gly
                465                 470                 475

aag tac gtg aat agt atg gag ctt gtc gac gca gat gag gat gg           1854
Lys Tyr Val Asn Ser Met Glu Leu Val Asp Ala Asp Glu Asp Gly
            480                 485                 490

gtaggtttat gcctaaaaga ttccgaatat cttctcattg acataaccag g gat cca    1911
                                                         Asp Pro

gtg gag act ttc cct atc gac gac tcg tat tcc cca gtt ttg cac cgg      1959
Val Glu Thr Phe Pro Ile Asp Asp Ser Tyr Ser Pro Val Leu His Arg
    495                 500                 505

att gac gcc gcc atc cgt gct cgg gct ata cat cct gac cag ccc ata      2007
Ile Asp Ala Ala Ile Arg Ala Arg Ala Ile His Pro Asp Gln Pro Ile
510                 515                 520                 525

cct cct cca tca gag aga ctg aca aaa ttc tca cac cca cga gag gat      2055
Pro Pro Pro Ser Glu Arg Leu Thr Lys Phe Ser His Pro Arg Glu Asp
                530                 535                 540

ctc atc gag aaa tca cag aaa cac cta gag aag ttg atc gag ata gcc      2103
Leu Ile Glu Lys Ser Gln Lys His Leu Glu Lys Leu Ile Glu Ile Ala
            545                 550                 555

gat gtt aag aag g gttggacatc accccacaat caagtctgtc agactgctaa       2156
Asp Val Lys Lys
        560

ttcagttacc ag tt  cct ccc aaa gcg aag ggt cgc aag cgc act cgt gaa    2206
              Val Pro Pro Lys Ala Lys Gly Arg Lys Arg Thr Arg Glu
                          565                 570
```

```
acc gaa aag cca ctt tcc gga ctc gac gtc gat gcc ctg ctt cat cat      2254
Thr Glu Lys Pro Leu Ser Gly Leu Asp Val Asp Ala Leu Leu His His
575                 580                 585                 590

gaa aag cgc gtc aag ata tct ccc aac aat gcc att cct gag ttc aag      2302
Glu Lys Arg Val Lys Ile Ser Pro Asn Asn Ala Ile Pro Glu Phe Lys
                595                 600                 605

cag act ctc gca cag gcc gag aat atc gag gcc atc aaa gac gct aca      2350
Gln Thr Leu Ala Gln Ala Glu Asn Ile Glu Ala Ile Lys Asp Ala Thr
            610                 615                 620

aag cag atg atg gtc atc gtt gaa gat caa atc aaa cac agt ctc ggt      2398
Lys Gln Met Met Val Ile Val Glu Asp Gln Ile Lys His Ser Leu Gly
        625                 630                 635

aat gct aac tac gac cgg gtc att gaa gcg ctg ggc acg atg cgt gac      2446
Asn Ala Asn Tyr Asp Arg Val Ile Glu Ala Leu Gly Thr Met Arg Asp
    640                 645                 650

gag ttg gta tct tac gaa gag cct gcc tcc tac aat gac ttc ctg ggc      2494
Glu Leu Val Ser Tyr Glu Glu Pro Ala Ser Tyr Asn Asp Phe Leu Gly
655                 660                 665                 670

cag ctc aag gat aag tta ctg cag gag aag ctt gga gga gac cga caa      2542
Gln Leu Lys Asp Lys Leu Leu Gln Glu Lys Leu Gly Gly Asp Arg Gln
                675                 680                 685

gag ctg tgg tgg ctt gtt cga cga aac aag ctg gga ctt gtc act cag      2590
Glu Leu Trp Trp Leu Val Arg Arg Asn Lys Leu Gly Leu Val Thr Gln
            690                 695                 700

cgc gag tcg gat caa tct agg gtt acc gat acg gaa gcc aaa gaa gta      2638
Arg Glu Ser Asp Gln Ser Arg Val Thr Asp Thr Glu Ala Lys Glu Val
        705                 710                 715

agt ctc act aag atg aag gag tga                                      2662
Ser Leu Thr Lys Met Lys Glu
    720                 725


<210> SEQ ID NO 12
<211> LENGTH: 725
<212> TYPE: PRT
<213> ORGANISM: Aspergillus oryzae

<400> SEQUENCE: 12

Met Ala Asp Lys Glu Ala Thr Val Tyr Ile Val Asp Val Gly Arg Ser
1               5                   10                  15

Met Gly Glu Cys Arg Asn Gly Arg Ser Val Thr Asp Leu Glu Trp Ala
            20                  25                  30

Met Gln Tyr Val Trp Asp Arg Ile Thr Gly Thr Val Ala Thr Gly Arg
        35                  40                  45

Lys Thr Ala Met Met Gly Val Ile Gly Leu Arg Thr Asp Glu Thr Ser
    50                  55                  60

Asn Glu Leu Glu Asp Asp Val His Phe Ser His Ile Ala Val Leu Ser
65                  70                  75                  80

Asn Leu Lys Gln Phe Leu Met Pro Asp Ile Arg Lys Leu Glu Asp Glu
                85                  90                  95

Leu Lys Pro Ser Lys Thr Asp Lys Gly Asp Ala Ile Ser Ala Ile Ile
            100                 105                 110

Leu Ala Ile Gln Met Ile Ile Thr His Cys Lys Lys Leu Lys Tyr Arg
        115                 120                 125

Arg Lys Ile Val Leu Val Thr Asn Gly Gln Gly Arg Met Ser Asp Glu
    130                 135                 140

Asp Leu Gly Glu Ile Val Lys Lys Val Lys Glu Asp Asn Ile Glu Leu
145                 150                 155                 160

Val Val Met Gly Ile Asp Phe Asp Asp Pro Glu Tyr Gly Tyr Lys Glu
                165                 170                 175
```

```
Glu Asp Lys Asp Pro His Lys Ala Glu Asn Glu Thr Leu Leu Arg Thr
            180                 185                 190

Leu Val Glu Asp Cys Asp Gly Val Tyr Gly Thr Phe Glu Gln Ala Val
        195                 200                 205

Ala Glu Leu Asp Ile Pro Arg Val Lys Ser Val Arg Ser Val Ala Ser
    210                 215                 220

Phe Lys Gly Tyr Leu Gln Leu Gly Asn Pro Glu Glu Tyr Asp Ser Ala
225                 230                 235                 240

Leu Arg Ile Pro Val Glu Arg Tyr Tyr Arg Thr Tyr Pro Ala Lys Pro
                245                 250                 255

Pro Thr Ala Ser Ser Phe Val Leu Arg Ser Glu Pro Glu Ala Gly Gln
            260                 265                 270

Glu Glu Ala Glu Ser Ser Glu Ala Ala Ala Ala Thr Gln Lys Gly Ser
        275                 280                 285

Gln Ser Gly Asp Ala Gly Leu Thr Thr Val Arg Thr Met Arg Thr Tyr
    290                 295                 300

Gln Val Glu Asp Lys Ser Ala Pro Gly Gly Lys Ile Asp Ile Glu Arg
305                 310                 315                 320

Asp Glu Leu Ala Lys Gly Tyr Glu Tyr Gly Arg Thr Ala Val His Ile
                325                 330                 335

Ser Glu Thr Asp Glu Asn Ile Thr Ile Leu Asp Thr Phe Ala Gly Leu
            340                 345                 350

Glu Leu Met Gly Phe Ile Gln Thr Asp Gln Tyr Gln Arg Tyr Met His
        355                 360                 365

Met Ser Asn Thr Asn Ile Ile Ile Ala Gln Arg Ala Asn Asp Lys Ala
    370                 375                 380

Ala Leu Ala Leu Ser Ser Phe Ile His Ala Leu Phe Glu Leu Glu Cys
385                 390                 395                 400

Tyr Ala Val Ala Arg Leu Val Val Lys Glu Asn Lys Pro Pro Val Ile
                405                 410                 415

Val Leu Leu Ala Pro Ser Ile Glu Pro Glu Tyr Glu Cys Leu Leu Glu
            420                 425                 430

Val Gln Leu Pro Phe Ala Glu Asp Val Arg Thr Tyr Arg Phe Pro Pro
        435                 440                 445

Leu Asp Lys Val Ile Thr Val Ser Gly Lys Val Val Thr Gln His Arg
    450                 455                 460

Asn Leu Pro Ser Asp Asp Leu Leu Asp Val Met Gly Lys Tyr Val Asn
465                 470                 475                 480

Ser Met Glu Leu Val Asp Ala Asp Glu Asp Gly Asp Pro Val Glu Thr
                485                 490                 495

Phe Pro Ile Asp Asp Ser Tyr Ser Pro Val Leu His Arg Ile Asp Ala
            500                 505                 510

Ala Ile Arg Ala Arg Ala Ile His Pro Asp Gln Pro Ile Pro Pro Pro
        515                 520                 525

Ser Glu Arg Leu Thr Lys Phe Ser His Pro Arg Glu Asp Leu Ile Glu
    530                 535                 540

Lys Ser Gln Lys His Leu Glu Lys Leu Ile Glu Ile Ala Asp Val Lys
545                 550                 555                 560

Lys Val Pro Pro Lys Ala Lys Gly Arg Lys Arg Thr Arg Glu Thr Glu
                565                 570                 575

Lys Pro Leu Ser Gly Leu Asp Val Asp Ala Leu Leu His His Glu Lys
            580                 585                 590

Arg Val Lys Ile Ser Pro Asn Asn Ala Ile Pro Glu Phe Lys Gln Thr
```

```
        595                 600                 605

Leu Ala Gln Ala Glu Asn Ile Glu Ala Ile Lys Asp Ala Thr Lys Gln
    610                 615                 620

Met Met Val Ile Val Glu Asp Gln Ile Lys His Ser Leu Gly Asn Ala
625                 630                 635                 640

Asn Tyr Asp Arg Val Ile Glu Ala Leu Gly Thr Met Arg Asp Glu Leu
                645                 650                 655

Val Ser Tyr Glu Glu Pro Ala Ser Tyr Asn Asp Phe Leu Gly Gln Leu
            660                 665                 670

Lys Asp Lys Leu Leu Gln Glu Lys Leu Gly Gly Asp Arg Gln Glu Leu
        675                 680                 685

Trp Trp Leu Val Arg Arg Asn Lys Leu Gly Leu Val Thr Gln Arg Glu
    690                 695                 700

Ser Asp Gln Ser Arg Val Thr Asp Thr Glu Ala Lys Glu Val Ser Leu
705                 710                 715                 720

Thr Lys Met Lys Glu
                725


<210> SEQ ID NO 13
<211> LENGTH: 32
<212> TYPE: DNA
<213> ORGANISM: Artificial Sequence
<220> FEATURE:
<223> OTHER INFORMATION: Synthetic PCR primer

<400> SEQUENCE: 13

ggtaccccag tacagtttca tgcaaagttc ta                                   32


<210> SEQ ID NO 14
<211> LENGTH: 33
<212> TYPE: DNA
<213> ORGANISM: Artificial Sequence
<220> FEATURE:
<223> OTHER INFORMATION: Synthetic PCR primer

<400> SEQUENCE: 14

ggatccttgg gggtagccat tgtttagatg tgt                                  33


<210> SEQ ID NO 15
<211> LENGTH: 29
<212> TYPE: DNA
<213> ORGANISM: Artificial Sequence
<220> FEATURE:
<223> OTHER INFORMATION: Synthetic PCR primer

<400> SEQUENCE: 15

gtcgacggcc agtaggaatc aggacagag                                       29


<210> SEQ ID NO 16
<211> LENGTH: 33
<212> TYPE: DNA
<213> ORGANISM: Artificial Sequence
<220> FEATURE:
<223> OTHER INFORMATION: Synthetic PCR primer

<400> SEQUENCE: 16

ctgcagccaa gcctgtcgtc ttgggctatt acg                                  33


<210> SEQ ID NO 17
<211> LENGTH: 28
<212> TYPE: DNA
<213> ORGANISM: Artificial Sequence
<220> FEATURE:
```

<223> OTHER INFORMATION: Synthetic PCR primer

<400> SEQUENCE: 17
ttgcacattt cctggcattg gtattcgg 28

<210> SEQ ID NO 18
<211> LENGTH: 26
<212> TYPE: DNA
<213> ORGANISM: Artificial Sequence
<220> FEATURE:
<223> OTHER INFORMATION: Synthetic PCR primer

<400> SEQUENCE: 18
aaatgcgaca gcacgtcctc ccttcc 26

<210> SEQ ID NO 19
<211> LENGTH: 32
<212> TYPE: DNA
<213> ORGANISM: Artificial Sequence
<220> FEATURE:
<223> OTHER INFORMATION: Synthetic PCR primer

<400> SEQUENCE: 19
gtcgacggat gagttggagc tgaagcgaat gg 32

<210> SEQ ID NO 20
<211> LENGTH: 32
<212> TYPE: DNA
<213> ORGANISM: Artificial Sequence
<220> FEATURE:
<223> OTHER INFORMATION: Synthetic PCR primer

<400> SEQUENCE: 20
ggatcctaat tgctgttagc agcgatactt ca 32

<210> SEQ ID NO 21
<211> LENGTH: 29
<212> TYPE: DNA
<213> ORGANISM: Artificial Sequence
<220> FEATURE:
<223> OTHER INFORMATION: Synthetic PCR primer

<400> SEQUENCE: 21
acatagacga ggaccaaaag tccctacag 29

<210> SEQ ID NO 22
<211> LENGTH: 28
<212> TYPE: DNA
<213> ORGANISM: Artificial Sequence
<220> FEATURE:
<223> OTHER INFORMATION: Synthetic PCR primer

<400> SEQUENCE: 22
ggcgttgtta gagggctttc gtccgttt 28

<210> SEQ ID NO 23
<211> LENGTH: 26
<212> TYPE: DNA
<213> ORGANISM: Artificial Sequence
<220> FEATURE:
<223> OTHER INFORMATION: Synthetic PCR primer

<400> SEQUENCE: 23
cggtggcttt ggttcgagag gtacga 26

<210> SEQ ID NO 24

<211> LENGTH: 32
<212> TYPE: DNA
<213> ORGANISM: Artificial Sequence
<220> FEATURE:
<223> OTHER INFORMATION: Synthetic PCR primer

<400> SEQUENCE: 24
gtggtctaga atgctcggca tgtctgcggt at 32

<210> SEQ ID NO 25
<211> LENGTH: 32
<212> TYPE: DNA
<213> ORGANISM: Artificial Sequence
<220> FEATURE:
<223> OTHER INFORMATION: Synthetic PCR primer

<400> SEQUENCE: 25
acagggtacc ccgtaaaatc gatattggaa ag 32

<210> SEQ ID NO 26
<211> LENGTH: 28
<212> TYPE: DNA
<213> ORGANISM: Artificial Sequence
<220> FEATURE:
<223> OTHER INFORMATION: Synthetic PCR primer

<400> SEQUENCE: 26
agaggcagac gatggaagat caggacca 28

<210> SEQ ID NO 27
<211> LENGTH: 30
<212> TYPE: DNA
<213> ORGANISM: Artificial Sequence
<220> FEATURE:
<223> OTHER INFORMATION: Synthetic PCR primer

<400> SEQUENCE: 27
agatctggta atgtgcccca ggcttgtcag 30

<210> SEQ ID NO 28
<211> LENGTH: 29
<212> TYPE: DNA
<213> ORGANISM: Artificial Sequence
<220> FEATURE:
<223> OTHER INFORMATION: Synthetic PCR primer

<400> SEQUENCE: 28
agatcttttc ccacaggttg gtgctagtc 29

<210> SEQ ID NO 29
<211> LENGTH: 35
<212> TYPE: DNA
<213> ORGANISM: Artificial Sequence
<220> FEATURE:
<223> OTHER INFORMATION: Synthetic PCR primer

<400> SEQUENCE: 29
ggggaattcc gcggccttta ccaaggtatc ggcga 35

<210> SEQ ID NO 30
<211> LENGTH: 31
<212> TYPE: DNA
<213> ORGANISM: Artificial Sequence
<220> FEATURE:
<223> OTHER INFORMATION: Synthetic PCR primer

<400> SEQUENCE: 30
agatctcatt ggtaacgaaa tgtaaaagct a 31

<210> SEQ ID NO 31
<211> LENGTH: 33
<212> TYPE: DNA
<213> ORGANISM: Artificial Sequence
<220> FEATURE:
<223> OTHER INFORMATION: Synthetic PCR primer

<400> SEQUENCE: 31
agatctgggg tgacgatgag ccgctcttgc atc 33

<210> SEQ ID NO 32
<211> LENGTH: 28
<212> TYPE: DNA
<213> ORGANISM: Artificial Sequence
<220> FEATURE:
<223> OTHER INFORMATION: Synthetic PCR primer

<400> SEQUENCE: 32
ggaacctgga cattctcact cctcgcgt 28

<210> SEQ ID NO 33
<211> LENGTH: 28
<212> TYPE: DNA
<213> ORGANISM: Artificial Sequence
<220> FEATURE:
<223> OTHER INFORMATION: Synthetic PCR primer

<400> SEQUENCE: 33
tctagacagc cacgaaggtt ttgccttt 28

<210> SEQ ID NO 34
<211> LENGTH: 26
<212> TYPE: DNA
<213> ORGANISM: Artificial Sequence
<220> FEATURE:
<223> OTHER INFORMATION: Synthetic PCR primer

<400> SEQUENCE: 34
tggatagctt tgcacgcgca agggtc 26

<210> SEQ ID NO 35
<211> LENGTH: 26
<212> TYPE: DNA
<213> ORGANISM: Artificial Sequence
<220> FEATURE:
<223> OTHER INFORMATION: Synthetic PCR primer

<400> SEQUENCE: 35
tgctttggca gcaggagcga acgcag 26

<210> SEQ ID NO 36
<211> LENGTH: 26
<212> TYPE: DNA
<213> ORGANISM: Artificial Sequence
<220> FEATURE:
<223> OTHER INFORMATION: Synthetic PCR primer

<400> SEQUENCE: 36
cttttaccga tgtgtgcacc gtgtct 26

<210> SEQ ID NO 37
<211> LENGTH: 26
<212> TYPE: DNA
<213> ORGANISM: Artificial Sequence
<220> FEATURE:

-continued

```
<223> OTHER INFORMATION: Synthetic PCR primer

<400> SEQUENCE: 37

gaaagccggg gcaccagtaa tcgcac                                           26


<210> SEQ ID NO 38
<211> LENGTH: 28
<212> TYPE: DNA
<213> ORGANISM: Artificial Sequence
<220> FEATURE:
<223> OTHER INFORMATION: Synthetic PCR primer

<400> SEQUENCE: 38

caacaccgtc ggttcttcca tcaagcgg                                         28


<210> SEQ ID NO 39
<211> LENGTH: 28
<212> TYPE: DNA
<213> ORGANISM: Artificial Sequence
<220> FEATURE:
<223> OTHER INFORMATION: Synthetic PCR primer

<400> SEQUENCE: 39

ggatgttgag ctcccacttg ccagtgtc                                         28


<210> SEQ ID NO 40
<211> LENGTH: 30
<212> TYPE: DNA
<213> ORGANISM: Artificial Sequence
<220> FEATURE:
<223> OTHER INFORMATION: Synthetic PCR primer

<400> SEQUENCE: 40

gaattctgtt ggtgggcttt tgcgtgtggt                                       30


<210> SEQ ID NO 41
<211> LENGTH: 30
<212> TYPE: DNA
<213> ORGANISM: Artificial Sequence
<220> FEATURE:
<223> OTHER INFORMATION: Synthetic PCR primer

<400> SEQUENCE: 41

cgagacggtc caggtccagg tctaggtctg                                       30
```